US012725286B2

(12) United States Patent
Nishimura

(10) Patent No.: US 12,725,286 B2
(45) Date of Patent: Sep. 1, 2026

(54) ENDOSCOPIC IMAGE PROCESSING APPARATUS AND ENDOSCOPIC IMAGE PROCESSING METHOD

(71) Applicant: OLYMPUS MEDICAL SYSTEMS CORP., Tokyo (JP)

(72) Inventor: Hirokazu Nishimura, Hachioji (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 325 days.

(21) Appl. No.: 18/236,572

(22) Filed: Aug. 22, 2023

(65) Prior Publication Data

US 2023/0410334 A1 Dec. 21, 2023

Related U.S. Application Data

(63) Continuation of application No. PCT/JP2021/007222, filed on Feb. 25, 2021.

(51) Int. Cl.
*G06T 7/50* (2017.01)
*A61B 1/00* (2006.01)
(Continued)

(52) U.S. Cl.
CPC ............ *G06T 7/50* (2017.01); *A61B 1/00009* (2013.01); *G06T 7/11* (2017.01);
(Continued)

(58) Field of Classification Search
CPC ... G06T 7/50; G06T 7/11; G06T 2207/10068; G06T 2207/20021; G06T 2207/20081;
(Continued)

(56) References Cited

U.S. PATENT DOCUMENTS 8,514,218 B2 * 8/2013 Hong ....................... A61B 1/04 600/101
2009/0048482 A1 2/2009 Hong et al.
(Continued)

FOREIGN PATENT DOCUMENTS

CN 101420897 A 4/2009
JP 3645223 B2 5/2005
(Continued)

OTHER PUBLICATIONS

Van der Stap, Nanda, Ferdinand van der Heijden, and Ivo AMJ Broeders. "Towards automated visual flexible endoscope navigation." Surgical Endoscopy 27.10 (2013): 3539-3547. (Year: 2013).*
(Continued)

*Primary Examiner* — Bobbak Safaipour
(74) *Attorney, Agent, or Firm* — Scully, Scott, Murphy & Presser, P.C.

(57) ABSTRACT

An image acquisition unit acquires an endoscopic image photographed by an endoscope. A segmentation unit partitions the endoscopic image into a plurality of regions. A depth information generator generates depth information indicating a depth of the endoscopic image. A recognition unit specifies a direction in which the endoscope is advanceable based on region information indicating a result of segmentation by the segmentation unit and depth information of the endoscopic image generated by the depth information generator.

11 Claims, 41 Drawing Sheets

(51) Int. Cl.
*G06T 7/11* (2017.01)
*H04N 23/50* (2023.01)

(52) U.S. Cl.
CPC ............... *G06T 2207/10068* (2013.01); *G06T 2207/20021* (2013.01); *G06T 2207/20081* (2013.01); *G06T 2207/20084* (2013.01); *G06T 2207/30028* (2013.01); *H04N 23/555* (2023.01)

(58) Field of Classification Search
CPC . G06T 2207/20084; G06T 2207/30028; A61B 1/00009; A61B 1/000096; A61B 1/000094; H04N 23/555
See application file for complete search history.

(56) References Cited

U.S. PATENT DOCUMENTS

| | | | | |
|---|---|---|---|---|
| 2022/0198742 | A1* | 6/2022 | Nishide .................. | G06V 10/82 |
| 2024/0423443 | A1* | 12/2024 | Oneyama ........... | A61B 1/00045 |

FOREIGN PATENT DOCUMENTS

| | | | |
|---|---|---|---|
| WO | 2008155828 | A1 | 12/2008 |
| WO | 2012/165204 | A1 | 12/2012 |
| WO | 2013/161589 | A1 | 10/2013 |
| WO | 2015/029318 | A1 | 3/2015 |
| WO | 2019155617 | A1 | 8/2019 |

OTHER PUBLICATIONS

International Preliminary Report on Patentability and Written Opinion of the International Searching Authority dated Aug. 29, 2023 received in PCT/JP2021/007222.

International Search Report dated May 18, 2021 received in PCT/JP2021/007222.

He., L., et al., Learning Depth from Single Images with Deep Neural Network Embedding Focal Length, Mar. 27, 2018, <URL:https://arxiv.org/pdf/1803.10039.pdf>.

Mahmood., F., et al., "Unsupervised Reverse Domain Adaptation for Synthetic Medical Images via Adversarial Tranining", Nov. 29, 2017, <URL:https://arxiv.org/pdf/1711.06606.pdf>.

Japanese Office Action dated Jul. 30, 2024 received in 2023-501930.

Japanese Office Action dated Nov. 26, 2024 received in 2023-501930.

Zhejiang University, Master's Thesis. "Development of 3D Endoscopy Video Processing Software based on Depth Map", Classification Code: TP392, Institution Code: 10335 Student No. 21315001.

Strap, et al., "Towards automated visual flexible endoscope navigation", Surg Endosc (2013) 27:3539-3547, DOI 10.1007/s00464-013-3003-7.

Chinese Office Action dated Jan. 29, 2026 received in 202180094476.4.

* cited by examiner

ENDOSCOPE CONTROL DEVICE
PROCESSING DEVICE
PROCESSOR
STORAGE MEDIUM
INPUT DEVICE
DISPLAY DEVICE
EXTERNAL FORCE INFORMATION ACQUISITION DEVICE
INSERTION SHAPE DETECTION DEVICE
1
2
10
11
12
13
14
16
17
18
20
22
24
30
40
50
60

<ENDOSCOPIC IMAGE>

<SEGMENTATION RESULT IMAGE>

<DEPTH ESTIMATION RESULT IMAGE>

<SUPERIMPOSED IMAGE>

<ENDOSCOPIC IMAGE>

<SEGMENTATION RESULT IMAGE>

<DEPTH ESTIMATION RESULT IMAGE>

<ENDOSCOPIC IMAGE>

<SEGMENTATION RESULT IMAGE>

<DEPTH ESTIMATION RESULT IMAGE>

<ENDOSCOPIC IMAGE>

<SEGMENTATION RESULT IMAGE>

<DEPTH ESTIMATION RESULT IMAGE>

<LABEL OF ANGLE OPERATION UPS>

<LABEL OF ANGLE OPERATION RIS>

<LABEL OF ANGLE OPERATION DOS>

<LABEL OF ANGLE OPERATION LES>

<LABEL OF ANGLE OPERATION URS>

<LABEL OF ANGLE OPERATION DRS>

<LABEL OF ANGLE OPERATION DLS>

<LABEL OF ANGLE OPERATION ULS>

<LABEL OF PUSHING OPERATION PSS>

<LABEL OF PULLING OPERATION PLS>

<LABEL OF SEARCH OPERATION SES>

〈SEGMENTATION RESULT IMAGE〉

〈ENDOSCOPIC IMAGE〉

〈SEGMENTATION RESULT IMAGE〉

〈ENDOSCOPIC IMAGE〉

〈SEGMENTATION RESULT IMAGE〉

〈ENDOSCOPIC IMAGE〉

<SEGMENTATION RESULT IMAGE>

<ENDOSCOPIC IMAGE>

<SEGMENTATION RESULT IMAGE>

<DEPTH ESTIMATION RESULT IMAGE>

ENDOSCOPIC IMAGE PROCESSING APPARATUS AND ENDOSCOPIC IMAGE PROCESSING METHOD

CROSS-REFERENCE TO RELATED APPLICATIONS

This application is based upon and claims the benefit of priority from the International Application No. PCT/JP2021/007222, filed on Feb. 25, 2021, the entire contents of which are incorporated herein by reference.

BACKGROUND

1. Field of the Disclosure

The present disclosure relates to a technique for processing an image captured by an endoscope.

2. Description of the Related Art

In endoscopic observation, an elongated flexible insertion portion is inserted into a subject to image the inside of the subject. In recent years, a research has been conducted to automate operations of the insertion portion, and Patent Literature 1 (JP 3645223 B2) discloses a technique for controlling a bending angle of a bent portion such that in an electronic endoscope apparatus provided with the bent portion bendable vertically and horizontally, a distal end portion of the insertion portion is directed to a center of a lumen which is being photographed.

In recent years, as a technique related to deep learning, a method for estimating information in a depth direction from an image has been proposed (Non Patent Literature 1: Lei He, Guanghui Wang and Zhanyi Hu, "Learning Depth from Single Images with Deep Neural Network Embedding Focal Length", 27 Mar. 2018 <URL:https://arxiv.org/pdf/1803.10039.pdf>), and a research on generation of information in the depth direction from an endoscopic image has also been conducted (Non Patent Literature 2: Faisal Mahmood, Richard Chen, Nicholas J. Durr, "Unsupervised Reverse Domain Adaptation for Synthetic Medical Images via Adversarial Training", 29 Nov. 2017 <URL:https://arxiv.org/pdf/1711.06606.pdf>).

In Patent Literature 1, the darkest part in a video output signal is determined as a lumen center, and the bending angle of the bent portion is controlled such that a distal end portion of an endoscope is directed to the center of the lumen. Therefore, a dark part that is in shadow by a structure (for example, a fold) projecting from the distal end portion of the endoscope may be determined as the lumen center and the distal end portion of the endoscope may be directed to the dark part. Further, even when the lumen center is accurately specified, there is a case where it is not preferable to advance the distal end portion of the endoscope toward the center of the lumen from situations around the distal end portion of the endoscope.

SUMMARY

The present disclosure has been made in view of the circumstances described above, and aims at providing a technique for generating appropriate information on motions or operations of an endoscope based on an endoscopic image.

An endoscopic image processing apparatus according to one aspect of the present disclosure includes: an image acquisition unit that acquires an endoscopic image photographed by an endoscope; a segmentation unit that partitions the endoscopic image acquired by the image acquisition unit into a plurality of regions; a depth information generator that generates depth information indicating a depth of the endoscopic image acquired by the image acquisition unit; and a recognition unit that specifies a direction in which the endoscope is advanceable based on region information indicating a result of segmentation by the segmentation unit and the depth information of the endoscopic image generated by the depth information generator.

An endoscopic image processing apparatus according to another aspect of the present disclosure includes: an image acquisition unit that acquires an endoscopic image photographed by an endoscope; an operation content selector that selects one or more operation contents from a plurality of predetermined operation contents based on the endoscopic image acquired by the image acquisition unit; a segmentation unit that partitions the endoscopic image acquired by the image acquisition unit into a plurality of regions; a recognition unit that recognizes situations around a distal end portion of the endoscope based on region information indicating a result of segmentation by the segmentation unit; and an operation content determiner that determines an operation content to be performed based on the operation content selected by the operation content selector and the situations recognized by the recognition unit.

A method of processing an endoscopic image according to still another aspect of the present disclosure includes: acquiring an endoscopic image photographed by an endoscope; partitioning the acquired endoscopic image into a plurality of regions; generating depth information indicating a depth of the acquired endoscopic image; and specifying a direction in which the endoscope is advanceable based on region information indicating a result of segmentation and the depth information of the endoscopic image.

Note that arbitrary combinations of the above components and modifications of the expressions of the present disclosure among methods, apparatuses, systems, recording media, computer programs, and the like are also effective as aspects of the present disclosure.

DETAILED DESCRIPTION

The disclosure will now be described by reference to the preferred embodiments. This does not intend to limit the scope of the present disclosure, but to exemplify the disclosure.

Hereinafter, embodiments of the present disclosure will be described with reference to the drawings.

Figure 1:
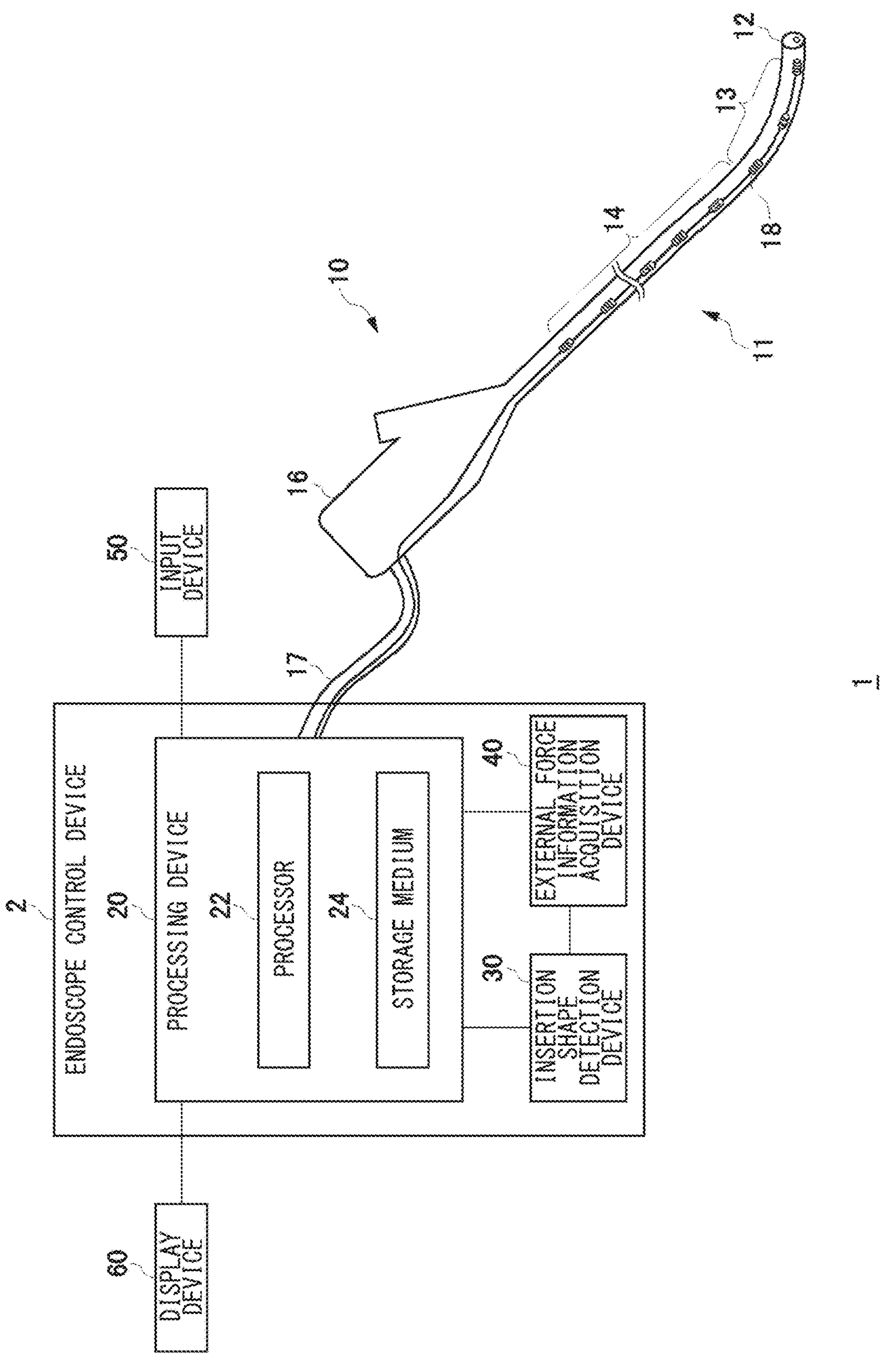
FIG. 1 is a diagram illustrating a configuration of an endoscope system according to an embodiment.

FIG. 1 illustrates a configuration of an endoscope system 1 according to an embodiment. The endoscope system 1 is provided in an endoscopic examination room and includes an endoscope control device 2, an endoscope 10, an input device 50, and a display device 60. The endoscope control device 2 includes a processing device 20, an insertion shape detection device 30, and an external force information acquisition device 40, and has a function of automatically operating the endoscope 10 inserted into the body of the subject. Automated operations of the endoscope 10 are performed by the processing device 20 that includes one or more processors 22 and a storage medium 24.

The input device 50 is an input interface operated by a user, and is configured to output an instruction in accordance with an operation of the user to the processing device 20. The input device 50 may include an operation device such as a mouse, a keyboard, and a touch panel. The display device 60 is a device that displays an endoscopic image or the like output from the processing device 20 on a screen, and may be a liquid crystal display or an organic EL display.

The endoscope 10 includes an imaging unit containing a solid-state imaging element (for example, a CCD image sensor or a CMOS image sensor). The solid-state imaging element converts incident light into an electric signal and outputs the electric signal to the processing device 20. The processing device 20 includes a signal processor that performs signal processing such as A/D conversion and noise removal on an imaging signal photoelectrically converted by the solid-state imaging element, and generates an endoscopic image. Note that the signal processor may be provided on a side of the endoscope 10, which may generate an endoscopic image. The processing device 20 causes the display device 60 to display an image photographed by the endoscope 10 in real time.

The endoscope 10 includes an insertion portion 11 to be inserted into the subject, an operation portion 16 provided on a proximal end side of the insertion portion 11, and a universal cord 17 extending from the operation portion 16. The endoscope 10 is detachably connected to the processing device 20 by a scope connector (not illustrated) provided at an end portion of the universal cord 17.

The insertion portion 11 having an elongated shape includes a distal end portion 12 that is hard, a bent portion 13 formed to be bendable, and a flexible tube portion 14 that is long and has flexibility in an order from a distal end side toward the proximal end side. Inside the distal end portion 12, the bent portion 13, and the flexible tube portion 14, a plurality of source coils 18 are disposed at predetermined intervals in a longitudinal direction of the insertion portion 11, and the source coil 18 generates a magnetic field in accordance with a coil drive signal supplied from the processing device 20.

When a user such as a physician operates a release switch of the operation portion 16 with the endoscope 10 inserted into the subject, the processing device 20 captures an endoscopic image, and transmits the endoscopic image to an image server (not illustrated) for recording. The release switch may be provided in the input device 50. A light guide (not illustrated) for transmitting illumination light supplied from the processing device 20 to illuminate the inside of the subject is provided inside the endoscope 10, and an illumination window for emitting the illumination light transmitted by the light guide to the subject and an imaging unit that photographs the subject at a predetermined cycle and outputs an imaging signal to the processing device 20 are provided at the distal end portion 12.

In the endoscope system 1 of the embodiment, the processing device 20 automatically operates the endoscope 10 to automatically control motions of the endoscope 10 in the subject, but it is also possible for the user to manually operate the endoscope 10 by gripping the operation portion 16.

The operation portion 16 may include an operation member for the user to operate the endoscope 10. The operation portion 16 includes at least an angle knob for bending the bent portion 13 in eight directions that intersect a longitudinal axis of the insertion portion 11.

Hereinafter, examples of basic operations of the endoscope 10 are illustrated.

"Advance operation (pushing operation)" for advancing the insertion portion 11

"Retraction operation (pulling operation)" for retracting the insertion portion 11

"Angle operation" for bending the bent portion 13

"Twist operation" for rotating the insertion portion 11 about an insertion axis "Air supply operation" for ejecting gas in front of the distal end portion 12

"Water supply operation" for jetting liquid in front of the distal end portion 12

"Suction operation" for sucking an object such as a tissue piece present near the distal end portion 12

"Search operation" for searching a lumen center by bending the bent portion 13 in a plurality of directions to direct the distal end portion 12 in a plurality of directions Note that, in the embodiment, an up-down direction of the distal end portion 12 is set as a direction orthogonal to an insertion axis of the insertion portion 11, and is set as a direction corresponding to a vertical direction of the solid-state imaging element provided in the imaging unit. Further, a left-right direction of the distal end portion 12 is set as a direction orthogonal to the insertion axis of the insertion portion 11, and is also set as a direction corresponding to a horizontal direction of the solid-state imaging element provided in the imaging unit. Therefore, in the embodiment, the up-down direction of the distal end portion 12 coincides with the up-down direction of the endoscopic image output from the signal processor 220, and the left-right direction of the distal end portion 12 coincides with the left-right direction of the endoscopic image.

The processing device 20 is detachably connected to each configuration of the insertion shape detection device 30, the external force information acquisition device 40, the input device 50, and the display device 60. The processing device 20 receives an instruction from the user input from the input device 50 and performs processing corresponding to the instruction. Further, the processing device 20 acquires an imaging signal periodically output from the endoscope 10 and causes the display device 60 to display an endoscopic image.

The insertion shape detection device 30 has a function of detecting the magnetic field generated by each of the plurality of source coils 18 provided in the insertion portion 11, and acquiring a position of the each of the plurality of source coils 18 based on an intensity of the detected magnetic field. The insertion shape detection device 30 generates insertion shape information indicating the acquired positions of the plurality of source coils 18, and outputs the insertion shape information to the processing device 20 and the external force information acquisition device 40.

The external force information acquisition device 40 stores data of curvature (or radius of curvature) and bending angle at a plurality of predetermined positions of the insertion portion 11 in a state where no external force is applied, and data of the curvature (or radius of curvature) and bending angle at the plurality of predetermined positions acquired in a state where a predetermined external force is applied to an arbitrary position of the insertion portion 11 from any assumed direction. The external force information acquisition device 40 specifies the positions of the plurality of source coils 18 provided in the insertion portion 11 based on the insertion shape information output from the insertion shape detection device 30, and acquires the curvature (or radius of curvature) and bending angle at the position of each of the plurality of source coils 18. The external force information acquisition device 40 may acquire external force information indicating the magnitude and direction of the external force at the position of each of the plurality of source coils 18 from the acquired curvature (or radius of curvature) and bending angle, and various data stored in advance. The external force information acquisition device 40 outputs the acquired external force information to the processing device 20.

Figure 2:
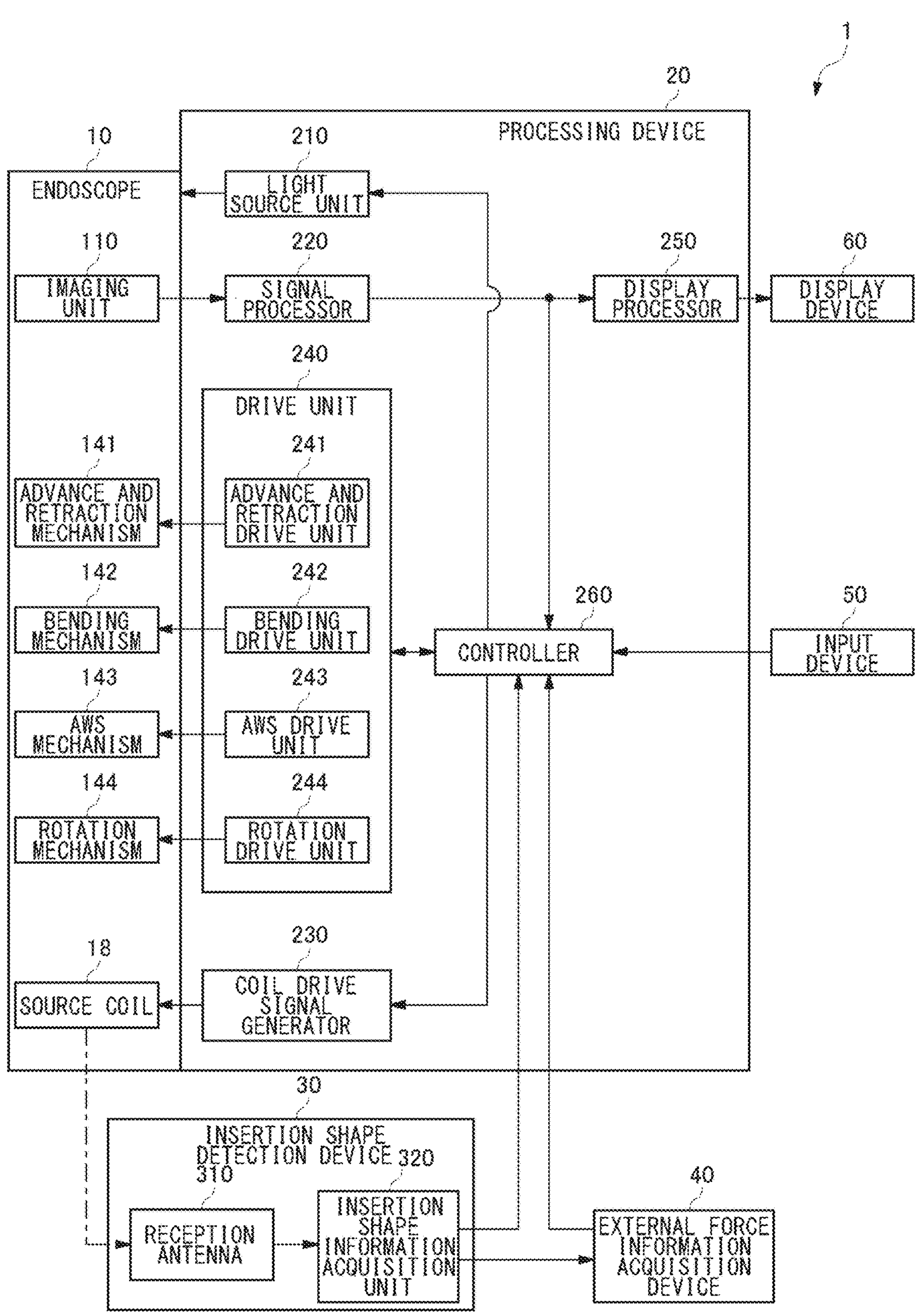
FIG. 2 is a diagram illustrating functional blocks of the endoscope system according to the embodiment.

FIG. 2 illustrates functional blocks of the endoscope system 1 according to the embodiment. The endoscope system 1 includes an endoscope 10, a processing device 20, an insertion shape detection device 30, an external force information acquisition device 40, an input device 50, and a display device 60.

The endoscope 10 includes a source coil 18, an imaging unit 110, an advance and retraction mechanism 141, a bending mechanism 142, an AWS mechanism 143, and a rotation mechanism 144. The advance and retraction mechanism 141, the bending mechanism 142, the AWS mechanism 143, and the rotation mechanism 144 constitute a motion mechanism in the endoscope 10.

The imaging unit 110 includes an observation window on which return light from a subject illuminated by illumination light is incident, and a solid-state imaging element (for example, a CCD image sensor or a CMOS image sensor) that photographs the return light and outputs an imaging signal.

The advance and retraction mechanism 141 has a mechanism for realizing a motion of advancing and retracting the insertion portion 11. For example, the advance and retraction mechanism 141 may be configured to have a pair of rollers disposed at positions facing each other with the insertion portion 11 interposed therebetween, and a motor that rotates the pair of rollers. The advance and retraction mechanism 141 executes one of a motion of advancing the insertion portion 11 and a motion of retracting the insertion portion 11 by driving the motor in accordance with an advance and retraction control signal output from the processing device 20 to rotate the pair of rollers.

The bending mechanism 142 has a mechanism for achieving a motion of bending the bent portion 13. For example, the bending mechanism 142 may be configured to have a plurality of bent pieces provided in the bent portion 13, a plurality of wires connected to the plurality of bent pieces, and a motor for pulling the plurality of wires. The bending mechanism 142 can bend the bent portion 13 in any of the eight directions that intersect the longitudinal axis of the insertion portion 11 by driving the motor in accordance with a bending control signal output from the processing device 20 to change a traction amount of the plurality of wires.

The AWS (Air feeding, Water feeding, and Suction) mechanism 143 has a mechanism for achieving an air supply motion, a water supply motion, and a suction motion. For example, the AWS mechanism 143 may be configured to have two pipelines of an air and water supply pipeline and a suction pipeline provided inside the insertion portion 11, the operation portion 16, and the universal cord 17, and a solenoid valve that performs a motion of opening one of the two pipelines while closing the other.

In a case where the solenoid valve is operated to open the air and water supply pipeline in accordance with an AWS control signal output from the processing device 20, the AWS mechanism 143 causes a fluid containing at least one of water and air supplied from the processing device 20 to flow through the air and water supply pipeline and discharges the fluid from a discharge port formed in the distal end portion 12. Further, in a case where the solenoid valve is operated to open the suction pipeline in accordance with the AWS control signal output from the processing device 20, the AWS mechanism 143 causes a suction force generated in the processing device 20 to act on the suction pipeline, and sucks an object present near a suction port formed at the distal end portion 12 by the suction force.

The rotation mechanism 144 has a mechanism for achieving a motion of rotating the insertion portion 11 with the insertion axis of the insertion portion 11 as a rotation axis. For example, the rotation mechanism 144 may be configured to have a support member that rotatably supports the insertion portion 11 on the proximal end side of the flexible tube portion 14, and a motor for rotating the support member. The rotation mechanism 144 rotates the insertion portion 11 about the insertion axis by driving the motor in accordance with a rotation control signal output from the processing device 20 to rotate the support member.

The insertion shape detection device 30 includes a reception antenna 310 and an insertion shape information acquisition unit 320. The reception antenna 310 is configured to have a plurality of coils that three-dimensionally detects the magnetic field generated by each of the plurality of source coils 18. When detecting the magnetic field generated by each of the plurality of source coils 18, the reception antenna 310 outputs a magnetic field detection signal corresponding to the intensity of the detected magnetic field to the insertion shape information acquisition unit 320.

The insertion shape information acquisition unit 320 acquires the position of each of the plurality of source coils 18 based on the magnetic field detection signal output from the reception antenna 310. Specifically, the insertion shape information acquisition unit 320 acquires, as the positions of the plurality of source coils 18, a plurality of three-dimensional coordinate values in a virtual spatial coordinate system having a predetermined position (such as the anus) of the subject as an origin or a reference point. The insertion shape information acquisition unit 320 generates insertion shape information containing three-dimensional coordinate values of the plurality of source coils 18, and outputs the insertion shape information to the controller 260 and the external force information acquisition device 40.

The external force information acquisition device 40 acquires the curvature (or radius of curvature) and bending angle at the position of each of the plurality of source coils 18 based on the insertion shape information output from the insertion shape detection device 30. The external force information acquisition device 40 may acquire external force information indicating the magnitude and direction of the external force at the position of each of the plurality of source coils 18 from the acquired curvature (or radius of curvature) and bending angle, and various data stored in advance. The external force information acquisition device 40 outputs the acquired external force information to the controller 260.

The processing device 20 includes a light source unit 210, a signal processor 220, a coil drive signal generator 230, a drive unit 240, a display processor 250, and a controller 260. In the embodiment, the processing device 20 serves as an image processing device that processes an endoscopic image. Specifically, the processing device 20 generates information on the motions or operations of the endoscope 10 based on the endoscopic image, and automatically controls the motions of the endoscope 10.

The light source unit 210 generates illumination light for illuminating the inside of the subject and supplies the illumination light to the endoscope 10. The light source unit 210 may include one or more LEDs or one or more lamps as a light source. The light source unit 210 may change a light amount of the illumination light in accordance with a motion control signal supplied from the controller 260.

The signal processor 220 includes a signal processing circuit, performs predetermined processing on the imaging signal output from the endoscope 10 to generate an endoscopic image, and outputs the generated endoscopic image to the display processor 250 and the controller 260.

The coil drive signal generator 230 generates a coil drive signal for driving the source coil 18. The coil drive signal generator 230 includes a drive circuit, generates a coil drive signal based on the motion control signal supplied from the controller 260, and supplies the coil drive signal to the source coil 18.

The drive unit 240 generates a control signal corresponding to the basic operation of the endoscope 10 based on the motion control signal supplied from the controller 260, and drives the motion mechanism of the endoscope 10. Specifically, the drive unit 240 controls at least one of an advance and retraction motion by the advance and retraction mechanism 141, a bending motion by the bending mechanism 142, an AWS motion by the AWS mechanism 143, and a rotation motion by the rotation mechanism 144. The drive unit 240 includes an advance and retraction drive unit 241, a bending drive unit 242, an AWS drive unit 243, and a rotation drive unit 244.

The advance and retraction drive unit 241 generates and outputs an advance and retraction control signal for controlling the motion of the advance and retraction mechanism 141 based on the motion control signal supplied from the controller 260. Specifically, the advance and retraction drive unit 241 generates and outputs an advance and retraction control signal for controlling rotation of the motor provided in the advance and retraction mechanism 141 based on the motion control signal supplied from the controller 260.

The bending drive unit 242 generates and outputs a bending control signal for controlling the motion of the bending mechanism 142 based on the motion control signal supplied from the controller 260. Specifically, the bending drive unit 242 generates and outputs a bending control signal for controlling the rotation of the motor provided in the bending mechanism 142 based on the motion control signal supplied from the controller 260.

The AWS drive unit 243 generates and outputs an AWS control signal for controlling the motion of the AWS mechanism 143 based on the motion control signal supplied from the controller 260. Specifically, the AWS drive unit 243 generates and outputs an AWS control signal for controlling a motion state of the solenoid valve provided in the AWS mechanism 143 based on the motion control signal supplied from the controller 260.

The rotation drive unit 244 generates and outputs a rotation control signal for controlling the motion of the rotation mechanism 144 based on the motion control signal supplied from the controller 260. Specifically, the rotation drive unit 244 generates and outputs a rotation control signal for controlling the rotation of the motor provided in the rotation mechanism 144 based on the motion control signal supplied from the controller 260.

The display processor 250 generates a display image including the endoscopic image output from the signal processor 220, and causes the display device 60 to display the generated display image. Note that the display processor 250 may cause the display device 60 to display a result image of the endoscopic image processed by the controller 260.

The controller 260 has a function of generating a motion control signal for causing the endoscope 10 to perform a motion in accordance with an instruction or the like from the operation portion 16 and the input device 50 and outputting the motion control signal to the drive unit 240 in a case where a manual insertion mode of the endoscope 10 is set to ON. Further, the controller 260 has a function of automatically controlling the motion of the endoscope 10 based on the endoscopic image generated by the signal processor 220 in a case where an automated insertion mode of the endoscope 10 is set to ON. Before describing automated operation control in the embodiment, manual operations of the endoscope by a physician will be described below.

In the manual insertion mode, the physician operates the endoscope based on various judgements. The physician views the endoscopic image, and instantly determines, for example, to avoid an obstacle present near the distal end portion of the endoscope, not to bring the distal end portion of the endoscope into contact with a mucosal surface, not to apply a load to an intestinal tract, and to determine a current route with a further route assumed, and operates the endoscope.

Figure 3A:
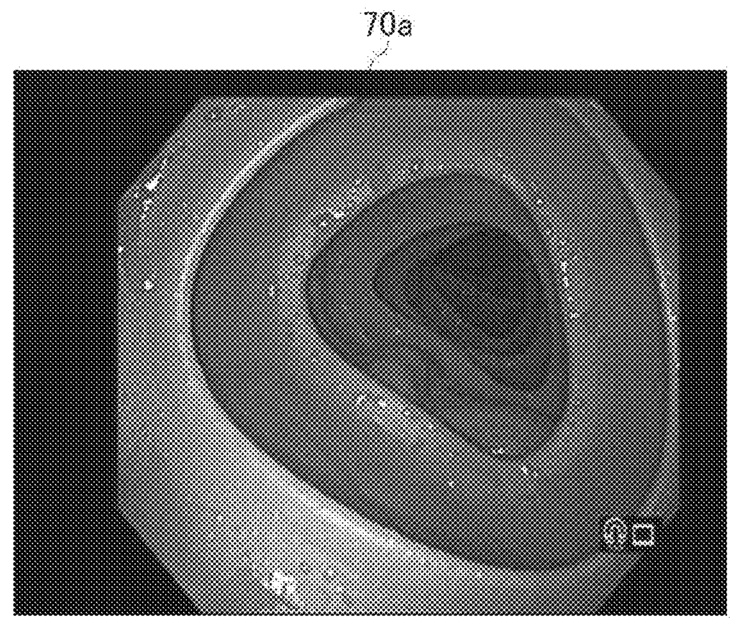
FIGS. 3(*a*) and 3(*b*) are views illustrating an example of an endoscopic image.
Figure 3B:
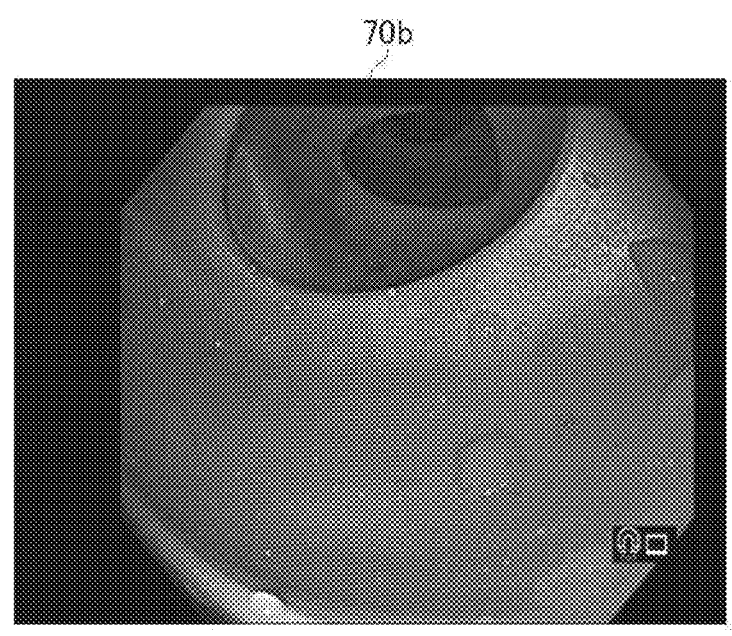

FIG. 3(*a*) illustrates an example of an endoscopic image. An endoscopic image 70*a* is an image obtained by photographing an intestinal tract (a rubber intestinal tract used for a colonoscopy phantom) formed of rubber with an endoscope. When the physician views the endoscopic image 70*a* and confirms that a lumen (that is, a center of the lumen, in other words, a lumen direction) exists in the center of the image, the physician determines that the distal end portion of the endoscope may be advanced, and advances the distal end portion of the endoscope forward.

FIG. 3(*b*) illustrates another example of the endoscopic image. Similarly, an endoscopic image 70*b* is an image obtained by photographing the rubber intestinal tract. The physician views the endoscopic image 70*b* to confirm that the lumen center exists in an upper portion of the image, and determines that the distal end portion of the endoscope is brought into contact with a fold in a central portion of the image when the distal end portion of the endoscope is advanced in this state. Therefore, the physician operates the angle knob so as to bend the bent portion 13 upward to allow the lumen center to be photographed at the center of the image. When the lumen center is photographed at the center of the image, a state similar to that of the endoscopic image 70*a* shown in FIG. 2(*a*) is obtained, so the physician determines that the distal end portion of the endoscope may be advanced, and advances the distal end portion of the endoscope forward.

The above determination and operation can be easily performed by a physician, and in order to achieve this by a device, it is necessary to recognize and grasp the situations around the distal end portion of the endoscope while specifying the lumen center from the endoscopic image. Therefore, in the embodiment, a technique for appropriately determining the motion of the endoscope 10 based on the endoscopic image is proposed.

Example 1

Figure 4:
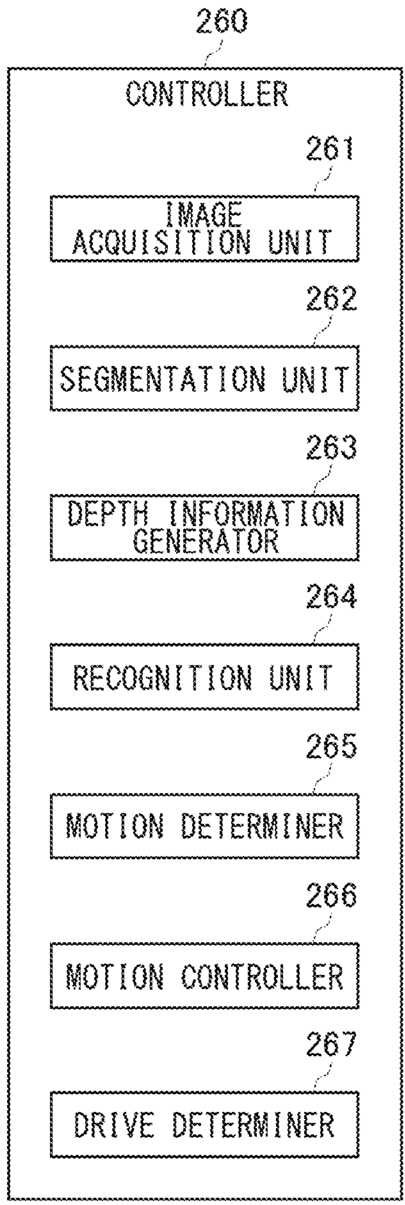
FIG. 4 is a diagram illustrating functional blocks of a controller according to Example 1.

FIG. 4 illustrates functional blocks of the controller 260 according to Example 1. The controller 260 includes an image acquisition unit 261, a segmentation unit 262, a depth information generator 263, a recognition unit 264, a motion determiner 265, a motion controller 266, and a drive determiner 267.

The controller 260 shown in FIG. 4 includes a computer or is a function of a computer, and various functions shown in FIG. 4 are implemented by the computer executing programs. The computer includes, as hardware, a memory for loading programs, one or more processors 22 for executing the loaded programs, an auxiliary storage device, other LSIs, and the like. The processor is composed of a plurality of electronic circuits including a semiconductor integrated circuit and an LSI, and the plurality of electronic circuits may be mounted on one chip or may be mounted on a plurality of chips. It should be understood by those skilled in the art that the functional blocks shown in FIG. 4 are implemented by cooperation of hardware and software, and therefore, these functional blocks can be implemented in various forms by only hardware, only software, or a combination thereof. For example, a program for executing at least some functions of the controller 260 may be stored in the storage medium 24, and the processor 22 may load the program from the storage medium 24 into a memory to implement each function of the controller 260.

The image acquisition unit 261 acquires an endoscopic image photographed by the endoscope 10 being inserted into the subject from the signal processor 220. The imaging unit 110 of the endoscope 10 supplies an imaging signal to the signal processor 220 at a predetermined cycle (for example, 30 frames/second), and the signal processor 220 generates an endoscopic image from the imaging signal and supplies the endoscopic image to the image acquisition unit 261. Therefore, the image acquisition unit 261 acquires an endoscopic image at a predetermined cycle. The image acquisition unit 261 supplies the acquired endoscopic image to the segmentation unit 262 and the depth information generator 263.

Segmentation Processing of Endoscopic Image

The segmentation unit 262 has a function of partitioning the endoscopic image acquired by the image acquisition unit 261 into a plurality of regions.

Specifically, the segmentation unit 262 executes semantic segmentation that labels each pixel in the endoscopic image, and partitions the endoscopic image into regions corresponding to a plurality of predetermined structures. The segmentation unit 262 defines a region having a structure of a type (a class) to be partitioned, and generates a segmentation result obtained by labeling pixels of various structures. Semantic segmentation is realized using a fully convolutional neural network (FCN), a bilateral segmentation network (BiSeNet), or the like, but the segmentation unit 262 according to Example 1 may execute semantic segmentation using the FCN.

As the type (the class) of the region to be partitioned, label values up to 0 to 255 may be prepared. In Example 1, label values are assigned to the following structures.

Label value 0: background pixel

Label value 1: normal lumen

Label value 2: fold edge (contour)

Label value 3: lumen of bent portion

Label value 4: fold edge of bent portion are set.

In semantic segmentation, the label value 0 generally means "a region not to be extracted", whereas the label value 0 defined in Example 1 means the mucosal surface. The "normal lumen" to which the label value 1 is assigned means a structure in which the endoscope can be advanced in the endoscopic image, and is defined as a structure indicating an advancing direction of the distal end portion of the endoscope. The structure specifically defined as "normal lumen" represents an extending direction of the lumen. Note that, in addition to these classes, classes may be set for structures such as residues, polyps, and blood vessels that appear in colonoscopy, and label values may be assigned to these classes, respectively.

Depth Information Generation Processing of Endoscopic Image

The depth information generator 263 has a function of generating information indicating the depth of the endoscopic image acquired by the image acquisition unit 261. Conventionally, various methods for estimating the depth of a pixel or a block included in an image have been proposed. Non Patent Literature 2 uses three-dimensional information by CT colonography as supervised data of distance information, but the depth information generator 263 may generate information indicating the depth of each pixel of the endoscopic image using the technique disclosed in Non Patent Literature 2.

Note that the depth information generator 263 may generate a learning model for depth estimation processing based on supervised data that has been simply created. For example, a creator of the supervised data may create the supervised data by visually designating each stage of the label values 0 to 4 in accordance with a positional relationship in a depth direction for each region of the image. In this case, a relative positional relationship in the depth direction based on human senses is obtained. Although it is not easy to obtain distance information as an absolute numerical value from a normal endoscopic image, it is easy for a person skilled in viewing an endoscopic image to sensuously determine that it is a near or distant view. In addition, the physician actually performs an insertion operation using the sensuous distance information obtained from the image, so that the supervised data created in this manner has high reliability, making it possible to generate a learning model capable of estimating an accurate depth.

In a depth estimation method by the depth information generator 263, a class is set in accordance with a distance range from the distal end portion 12 of the endoscope. In Example 1, a label value is assigned to each distance range.

Label value 0: depth<first distance

Label value 1: first distance≤depth<second distance

Label value 2: second distance≤depth<third distance

Label value 3: third distance≤depth<fourth distance

Label value 4: fourth distance≤depth

The label value 0 means a region having the shortest distance from the distal end portion 12, and the label value 4 means a region having the farthest distance from the distal end portion 12.

Figure 5:
FIG. 5 is a view illustrating an example of an endoscopic image.

FIG. 5 illustrates an example of an endoscopic image. The endoscopic image has a size of 720×480, and each pixel of RGB is represented by eight bits. In this endoscopic image, the lumen is linearly photographed in the depth direction, and a plurality of folds surround the lumen. Among them, the fold photographed at a lower right exist at a distance close to the distal end portion of the endoscope.

When acquiring an endoscopic image photographed by the endoscope 10 from the signal processor 220, the image acquisition unit 261 supplies the endoscopic image to the segmentation unit 262 and the depth information generator 263. The segmentation unit 262 executes semantic segmentation to partition the endoscopic image into a plurality of regions. At the same time, the depth information generator 263 executes the depth estimation processing to generate depth information indicating the depth of the endoscopic image.

Figure 6:
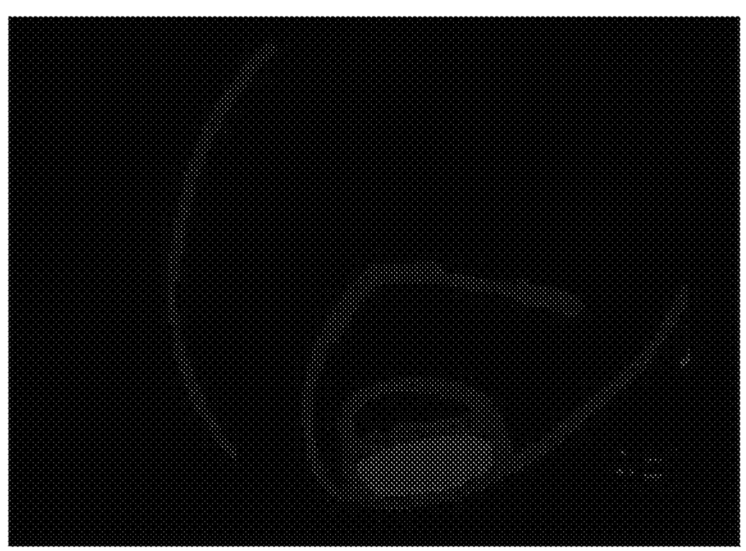
FIG. 6 is a diagram illustrating an example of a segmentation result.

FIG. 6 illustrates an example of a segmentation result by the segmentation unit 262. The segmentation unit 262 partitions the endoscopic image into a plurality of regions and derives region information indicating a result of segmentation. Here, the region information may be derived as a label value of each pixel related to the structure. In Example 1, the segmentation unit 262 generates a segmentation result image using the derived label value. As will be described later, the segmentation result image may be displayed on the display device 60 and presented to the user.

The segmentation unit 262 may set the pixel value of (R,G,B) corresponding to the label value of the partitioned region as follows. Note that, in the following description, in order to distinguish it from the label value related to the depth information, the label values 0 to 4 of the partitioned region are expressed as label values a0 to a4.

Label value a0 (background pixel)→(0,0,0)

Label value a1 (normal lumen)→(128,0,0)

Label value a2 (fold edge)→(0,0,128)

Label value a3 (lumen of bent portion)→(192,0,0)

Label value a4 (fold edge of bent portion)→(128, 128, 128)

With the pixel values set in this manner, the segmentation unit 262 generates a segmentation result image in which the mucosal surface occupying a large part (label value e0) is painted in black and the extracted structural part is painted in color. The segmentation unit 262 supplies the segmentation result image to the recognition unit 264 as the region information indicating the result of the segmentation. In the example shown in FIG. 6, a region of fold edges having a concentric shape and a region of the normal lumen are displayed so as to be visible to the user. Note that, in another example, the segmentation unit 262 may supply the label value of each pixel to the recognition unit 264 as the region information indicating the result of the segmentation.

Figure 7:
FIG. 7 is a diagram illustrating an example of a depth information estimation result.

FIG. 7 illustrates an example of a depth information estimation result by the depth information generator 263. The depth information generator 263 executes the depth estimation processing on the endoscopic image and generates the depth information indicating the depth of the endoscopic image. Here, the depth information may be derived as a label value of each pixel related to the depth (the distance from the distal end portion of the endoscope). In Example 1, the depth information generator 263 generates a depth estimation result image using the derived label value. As will be described later, the depth estimation result image may be displayed on the display device 60 together with the segmentation result image and presented to the user.

The depth information generator 263 may set the pixel value of (R,G,B) corresponding to the label value that represents a level of the depth as follows. Note that, in the following description, the label values 0 to 4 of the depth information are expressed as label values d0 to d4 in order to distinguish them from the label value related to the partitioned region.

Label value d0 (less than first distance)→(40,0,0)

Label value d1 (first distance or more and less than second distance)→(80,0,0)

Label value d2 (second distance or more and less than third distance)→(120,0,0)

Label value d3 (third distance or more and less than fourth distance)→(160,0,0)

Label value d4 (fourth distance or more)→(200,0,0)

With the pixel values set in this manner, the depth information generator 263 generates a depth estimation result image in which a deeper region is colored in bright red. The depth information generator 263 supplies the depth estimation result image to the recognition unit 264 as the depth information of the endoscopic image. Note that, in another example, the depth information generator 263 may supply the label value of each pixel to the recognition unit 264 as the depth information of the endoscopic image.

The recognition unit 264 receives the region information of the endoscopic image from the segmentation unit 262, receives the depth information of the endoscopic image from the depth information generator 263, and recognizes the situations around the distal end portion of the endoscope. Specifically, the recognition unit 264 recognizes the structure such as the lumen direction and the fold included in the endoscopic image together with the positional relationship in the depth direction using the region information and the depth information.

Figure 8:
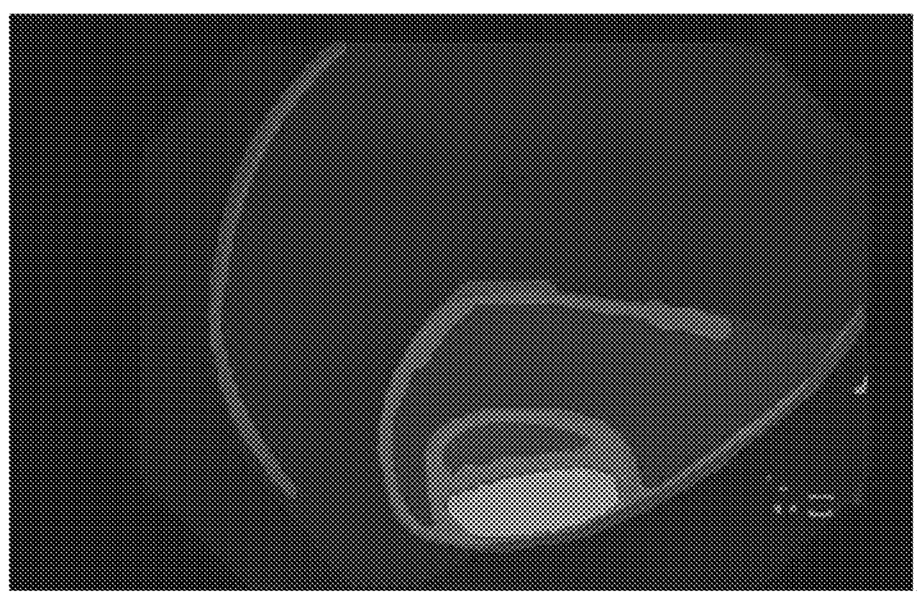
FIG. 8 is a diagram illustrating an example of a superimposed image in which the segmentation result image and the depth estimation result image are superimposed.

FIG. 8 illustrates an example of a superimposed image in which the segmentation result image and the depth estimation result image are superimposed. In a case where the segmentation result image and the depth estimation result image are generated with high accuracy, the fold edge extracted in the segmentation result image and a boundary line shown in the depth estimation result image basically match. In addition, a normal lumen region extracted in the segmentation result image and the deepest region shown in the depth estimation result image basically coincide with each other. The recognition unit 264 can recognize at what depth in the depth direction each of the regions corresponding to various structures partitioned by the segmentation unit 262 is located from the superimposed image.

Next, recognition of various structures with the positional relationship in the depth direction will be described.

Figure 9:
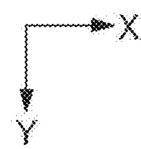
FIG. 9 is a diagram illustrating an example of a recognition result in the superimposed image.
Figure 9:
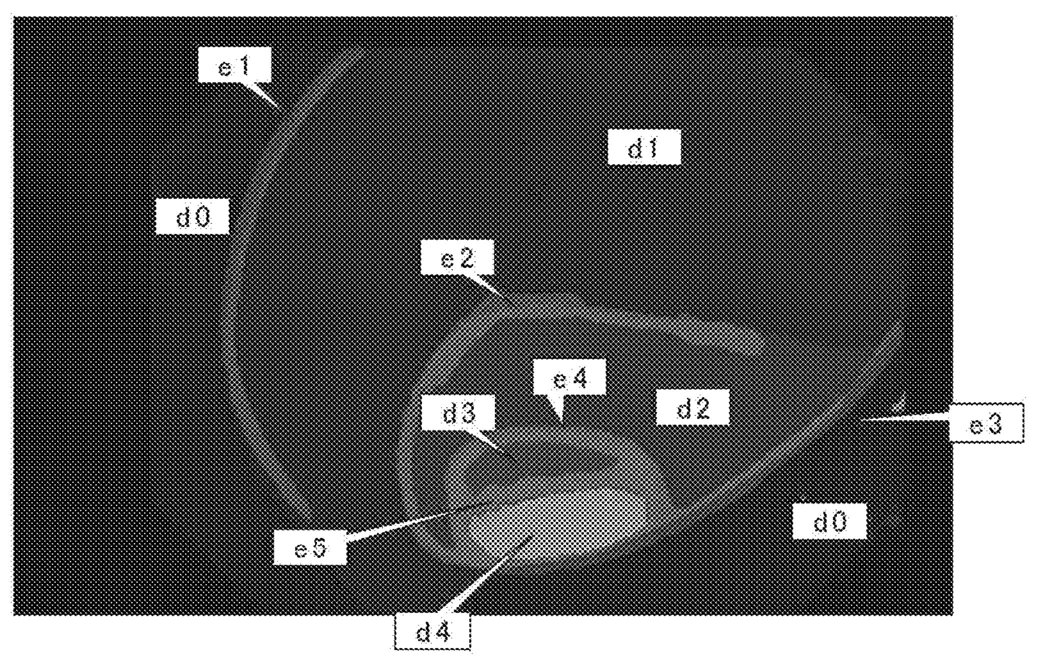

FIG. 9 illustrates an example of a recognition result in the superimposed image shown in FIG. 8. In the superimposed image shown in FIG. 9, label values d0 to d4 are added to the region as information related to the depth direction. Further, a reference sign of e1 to e5 is assigned to a region (label value a2) extracted as a fold edge by the segmentation unit 262.

Referring to the segmentation result image shown in FIG. 6, since fold edges e2, e3, and e4 are continuous, one reference sign is allocated to the fold edges e2, e3, and e4 based only on the information of the segmentation result image. However, the recognition unit 264 can recognize that the fold edges e2, e3, and e4 are different from each other by specifying the label values d0 to d4 related to the depth of each pixel with reference to the depth information of the endoscopic image. Note that, in a case where the fold edge exists at a boundary of different label values related to the depth, the recognition unit 264 preferably applies a shallower label value.

A method of recognizing a situation of an arbitrary pixel p(x,y) will be described. Note that $0 \leq x < 720$ and $0 \leq y < 480$ are satisfied. For the pixel p(x,y), it is assumed that the label value pa(x,y) related to the segmentation is “a2” and the label value pd(x,y) related to the depth is “d0”. Here, the label value a2 indicates a fold edge, and the label value d0 indicates a region estimated to be closest to the distal end portion of the endoscope in the depth direction. The recognition unit 264 recognizes that such a pixel p is a pixel constituting a fold edge e1 or e3. Further, since the region d0 includes the fold edges e1 and e3, the recognition unit 264 recognizes that the region d0 is a region obtained by photographing the mucosal surface including the fold. The label values pd(x,y) related to the depths of fold edges e2, e4, and e5 are “d1”, “d2”, and “d3”, respectively, and thus, the recognition unit 264 recognizes that the regions d1, d2, and d3 are also regions obtained by photographing the mucosal surface including folds having different depths.

The recognition unit 264 specifies a pixel p(x,y) that has a label value d4 indicating the deepest region, and refers to a label value pa(x,y) related to the segmentation allocated to the pixel p(x,y). At this time, when the region having the label value d4 and the region having the label value a1 substantially coincide with each other, the recognition unit 264 recognizes that the region having the label value d4 and the label value a1 is the deepest and indicates a structure indicating the advancing direction. Further, since the fold edge e3 that is the boundary of the deepest region of the label value d4 belongs to the shallowest region of the label value d0, the recognition unit 264 recognizes that a fold that may be an obstacle to the advancing motion of the distal end portion of the endoscope exists in the lower right of the image. In other words, the recognition unit 264 recognizes that the direction shown in the lower right of the image is a direction in which the endoscope should not be advanced.

As described above, the recognition unit 264 recognizes various structures included in the endoscopic image together with the positional relationship in the depth direction based on the region information indicating the result of the segmentation by the segmentation unit 262 and the depth information of the endoscopic image generated by the depth information generator 263. As a result, the recognition unit 264 specifies a direction in which the endoscope can be advanced and a direction in which the endoscope should not be advanced, and specifies an existence position of a structure that can be an obstacle when the endoscope is advanced. The recognition unit 264 supplies information indicating these recognition results to the motion determiner 265.

The motion determiner 265 generates information on the advancing direction of the endoscope 10 based on the recognition results in the recognition unit 264. Specifically, the motion determiner 265 may generate information on the advancing direction of the endoscope 10 from the direction in which the distal end portion of the endoscope can be advanced and the direction in which the distal end portion of the endoscope should not be advanced. In this example, the motion determiner 265 may generate information on the advancing direction of the endoscope 10 so as to advance the distal end portion 12 upward while avoiding a fold that exists in front of the deepest normal lumen region.

Figure 10:
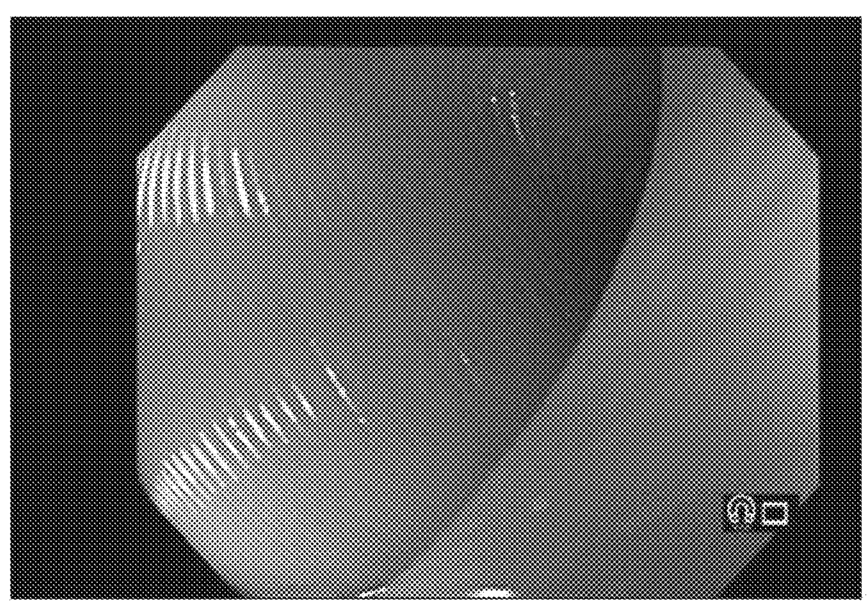
FIG. 10 is a view illustrating another example of an endoscopic image.

FIG. 10 illustrates another example of an endoscopic image. In this endoscopic image, a bent portion of the large intestine is photographed. When acquiring an endoscopic image photographed by the endoscope 10 from the signal processor 220, the image acquisition unit 261 supplies the endoscopic image to the segmentation unit 262 and the depth information generator 263. The segmentation unit 262 partitions the endoscopic image into a plurality of regions and generates a segmentation result image. At the same time, the depth information generator 263 executes the depth estimation processing to generate depth information indicating the depth of the endoscopic image, and generates a depth estimation result image based on the depth information.

Figure 11:
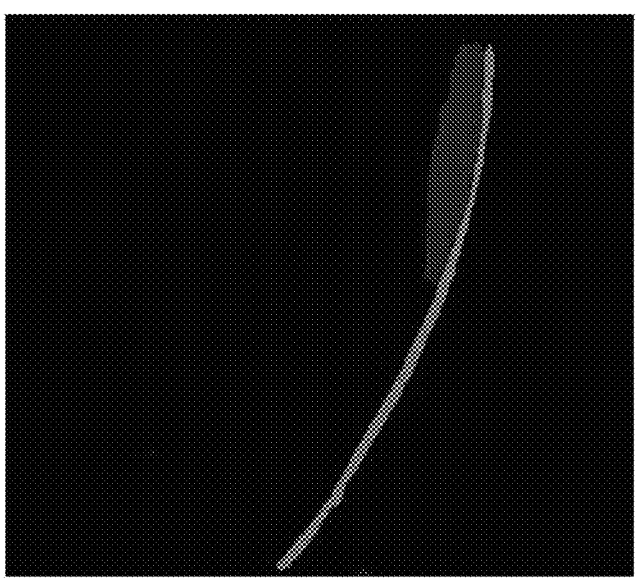
FIG. 11 is a diagram illustrating an example of a segmentation result.

FIG. 11 illustrates an example of a segmentation result by the segmentation unit 262. The segmentation unit 262 partitions the endoscopic image into a plurality of regions and derives region information indicating a result of segmentation. The region information is derived as a label value pa(x,y) of each pixel related to the structure, and the segmentation unit 262 generates a segmentation result image using the derived label value. The segmentation result image includes a region of the fold edge of the bent portion that extends in the longitudinal direction near the center and a region of the lumen of the bent portion that is extracted along the upper portion of the fold edge of the bent portion. The segmentation unit 262 supplies the segmentation result image to the recognition unit 264 as the region information indicating the result of the segmentation.

Figure 12:
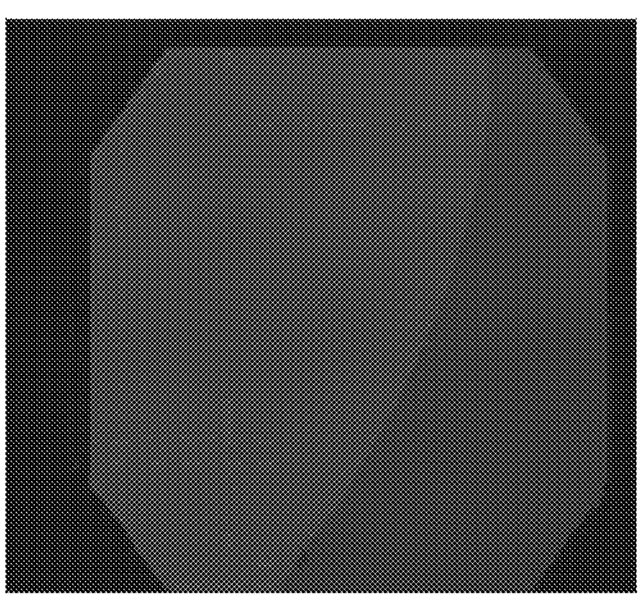
FIG. 12 is a diagram illustrating an example of a depth information estimation result.

FIG. 12 illustrates an example of a depth information estimation result by the depth information generator 263. The depth information generator 263 executes the depth estimation processing on the endoscopic image and generates the depth information indicating the depth of the endoscopic image. The depth information is derived as a label value pd(x,y) of each pixel related to the depth, and the depth information generator 263 generates a depth estimation result image using the derived label value. The depth information generator 263 supplies the depth estimation result image to the recognition unit 264 as the depth information of the endoscopic image.

The recognition unit 264 receives the region information of the endoscopic image from the segmentation unit 262, receives the depth information of the endoscopic image from the depth information generator 263, and recognizes the situations around the distal end portion of the endoscope. Specifically, the recognition unit 264 recognizes the structure such as the lumen direction and the fold included in the endoscopic image together with the positional relationship in the depth direction using the region information and the depth information. As a result, the recognition unit 264 specifies the existence position of the structure that can be an obstacle when the endoscope is advanced, and specifies the direction in which the endoscope can be advanced and the direction in which the endoscope should not be advanced. In this example, the recognition unit 264 recognizes that a left side of the image is the direction in which the endoscope can be advanced and a right side of the image is the direction in which the endoscope should not be advanced, and recognizes that the lumen continues in a right direction. The recognition unit 264 supplies the recognition result to the motion determiner 265, and the motion determiner 265 generates information on the advancing direction of the endoscope based on the direction in which the endoscope can be advanced and the direction in which the endoscope should not be advanced. Specifically, the motion determiner 265 determines the advancing direction of the distal end portion of the endoscope so that the distal end portion of the endoscope is directed to the left and advanced in the directed direction.

Figure 13:
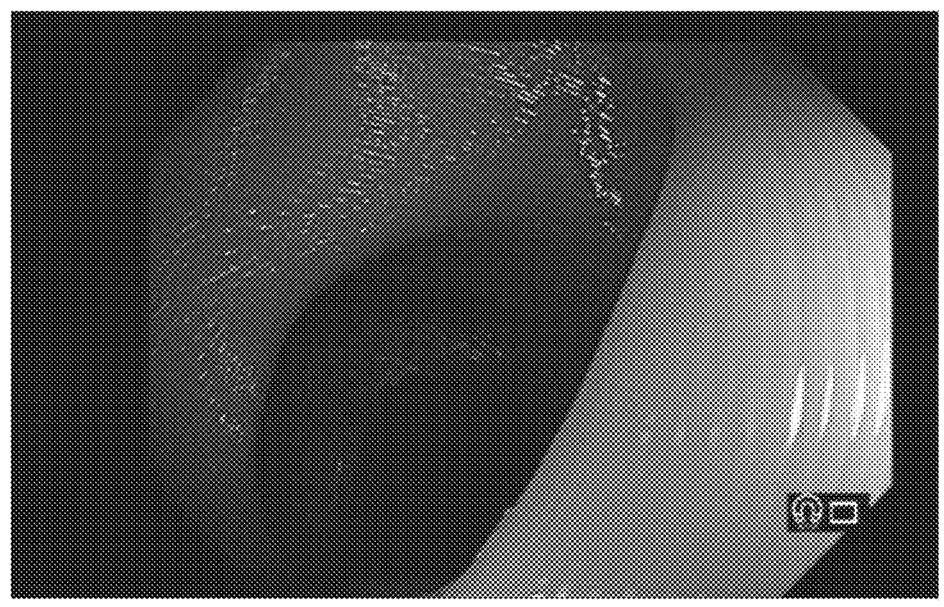
FIG. 13 is a view illustrating another example of an endoscopic image.

FIG. 13 illustrates another example of an endoscopic image. In this endoscopic image, a large fold is photographed on the right side. Upon acquisition of an endoscopic image from the signal processor 220, the image acquisition unit 261 supplies the endoscopic image to the segmentation unit 262 and the depth information generator 263.

Figure 14:
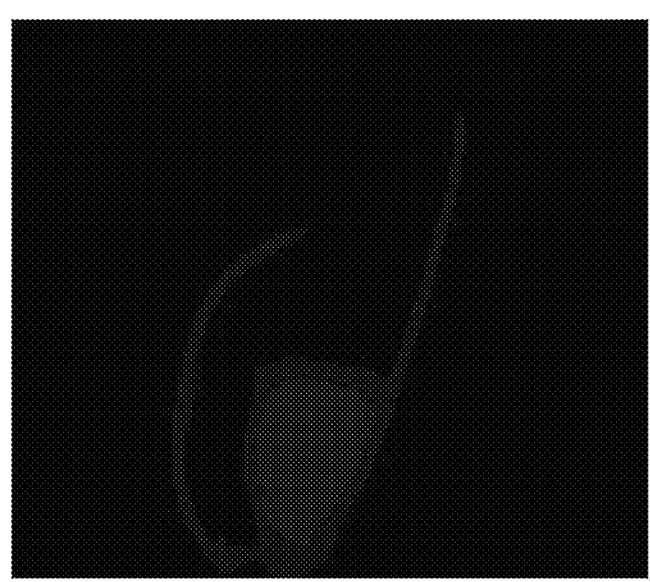
FIG. 14 is a diagram illustrating an example of a segmentation result.

FIG. 14 illustrates an example of a segmentation result by the segmentation unit 262. The segmentation unit 262 partitions the endoscopic image into a plurality of regions, derives region information indicating the result of the segmentation, and generates a segmentation result image. The segmentation result image includes a region of a fold edge and a region of a normal lumen. The segmentation unit 262 supplies the segmentation result image to the recognition unit 264 as the region information indicating the result of the segmentation.

Figure 15:
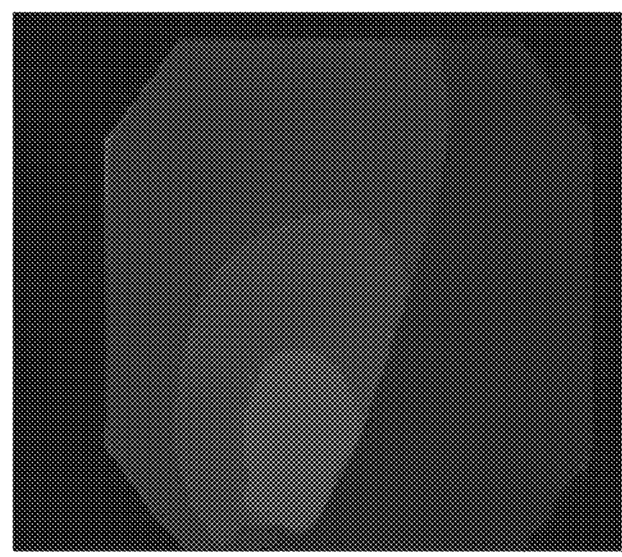
FIG. 15 is a diagram illustrating an example of a depth information estimation result.

FIG. 15 illustrates an example of a depth information estimation result by the depth information generator 263. The depth information generator 263 executes the depth estimation processing on the endoscopic image to generate depth information indicating the depth of the endoscopic image, and generates a depth estimation result image. The depth information generator 263 supplies the depth estimation result image to the recognition unit 264 as the depth information of the endoscopic image.

The recognition unit 264 receives the region information of the endoscopic image from the segmentation unit 262, receives the depth information of the endoscopic image from the depth information generator 263, and recognizes the situations around the distal end portion of the endoscope. In this example, the recognition unit 264 recognizes that a large fold exists on the right side of the image, which hinders the advancing motion of the endoscope, and recognizes that the left side of the image is the direction in which the endoscope can be advanced and the right side of the image is the direction in which the endoscope should not be advanced. The recognition unit 264 supplies the recognition result to the motion determiner 265, and the motion determiner 265 generates information on the advancing direction of the endoscope based on the direction in which the endoscope can be advanced and the direction in which the endoscope should not be advanced. Specifically, the motion determiner 265 determines the advancing direction of the distal end portion of the endoscope so that the distal end portion of the endoscope is directed to the left and advanced in the directed direction.

Figure 16:
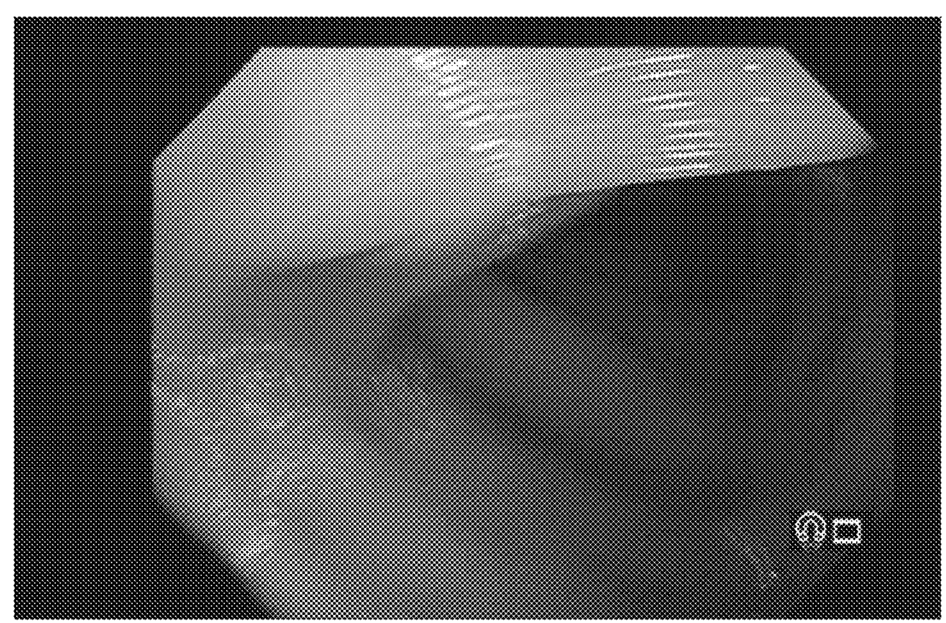
FIG. 16 is a view illustrating another example of an endoscopic image.

FIG. 16 illustrates another example of an endoscopic image. In this endoscopic image, a large fold are photographed from an upper side to the left side. Upon acquisition of an endoscopic image from the signal processor 220, the image acquisition unit 261 supplies the endoscopic image to the segmentation unit 262 and the depth information generator 263.

Figure 17:
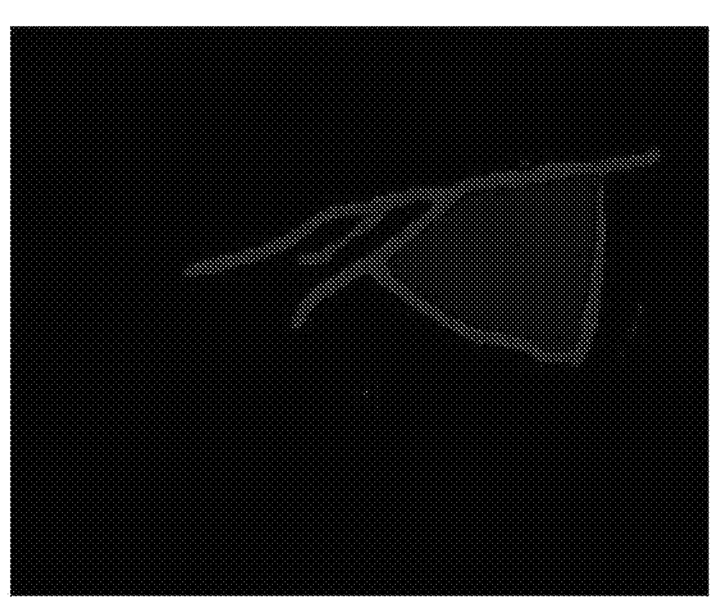
FIG. 17 is a diagram illustrating an example of a segmentation result.

FIG. 17 illustrates an example of a segmentation result by the segmentation unit 262. The segmentation unit 262 partitions the endoscopic image into a plurality of regions, derives region information indicating the result of the segmentation, and generates a segmentation result image. The segmentation result image includes a region of a fold edge and a region of a normal lumen. The segmentation unit 262 supplies the segmentation result image to the recognition unit 264 as the region information indicating the result of the segmentation.

Figure 18:
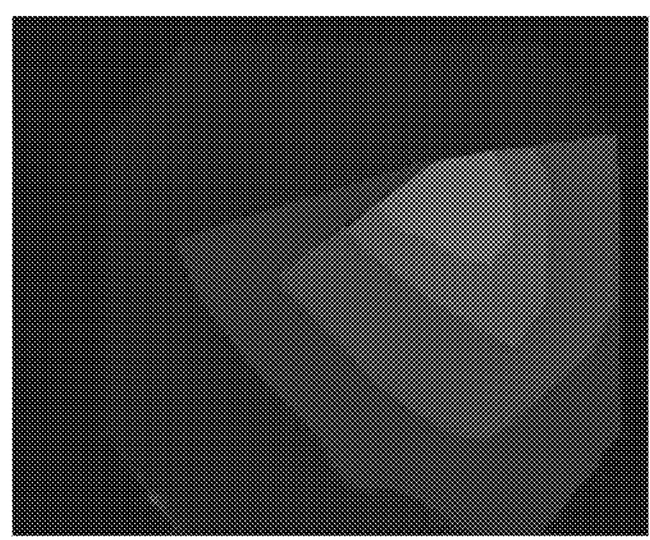
FIG. 18 is a diagram illustrating an example of a depth information estimation result.

FIG. 18 illustrates an example of a depth information estimation result by the depth information generator 263. The depth information generator 263 executes the depth estimation processing on the endoscopic image to generate depth information indicating the depth of the endoscopic image, and generates a depth estimation result image. The depth information generator 263 supplies the depth estimation result image to the recognition unit 264 as the depth information of the endoscopic image.

The recognition unit 264 receives the region information of the endoscopic image from the segmentation unit 262, receives the depth information of the endoscopic image from the depth information generator 263, and recognizes the situations around the distal end portion of the endoscope. Comparing the segmentation result image shown in FIG. 17 with the depth estimation result image shown in FIG. 18, the region extracted as the normal lumen (label value a1) in the segmentation result image spans the regions of the label values d3 and d4 in the depth estimation result image. Therefore, the recognition unit 264 specifies an overlapping region between the region of the label value a1 in the segmentation result image and the region of the label value d4 in the depth estimation result image as a region where the endoscope can be advanced. The recognition unit 264 supplies the recognition result to the motion determiner 265, and the motion determiner 265 generates information on the advancing direction of the endoscope. Specifically, the motion determiner 265 determines the advancing direction of the distal end portion of the endoscope so that the distal end portion of the endoscope is directed rightward and advanced in the directed direction.

In Example 1, the motion determiner 265 may determine a motion content of the endoscope 10 at each timing at which the image acquisition unit 261 acquires an endoscopic image, and the motion controller 266 may generate a motion control signal in accordance with the determined motion content and supply the motion control signal to the drive unit 240.

Note that, as another timing example, the drive unit 240 may drive the motion mechanism of the endoscope 10 based on the motion control signal by the motion controller 266, at the timing when the drive is terminated, the motion determiner 265 may determine the motion content of the endoscope 10, and the motion controller 266 may generate the motion control signal.

For example, when the drive unit 240 drives the motion mechanism of the endoscope 10, the drive determiner 267 determines that the drive unit 240 is driving the motion mechanism. When the drive by the drive unit 240 is terminated, the drive determiner 267 determines that the drive of the motion mechanism has been ended. At this time, the drive determiner 267 notifies the recognition unit 264 that a new motion content should be determined. The recognition unit 264 generates recognition results of various structures included in the endoscopic image, and the motion determiner 265 determines the motion content of the endoscope 10 based on the recognition results. The motion determiner 265 may determine the motion content of the endoscope 10 after or immediately before the drive of the motion mechanism is completed.

In Example 1, a segmentation processing result by the segmentation unit 262 and a depth estimation processing result by the depth information generator 263 may be corrected by various known techniques using frequency component information, brightness information of pixel values, and the like, and then provided to the recognition unit 264.

The motion controller 266 has a function of controlling the motion of the endoscope 10 based on the motion content determined by the motion determiner 265. The motion controller 266 may set a motion amount in the determined motion content based on at least one of the insertion shape information output from the insertion shape detection device 30 and the external force information output from the external force information acquisition device 40. The motion controller 266 generates a motion control signal corresponding to the motion content determined by the motion determiner 265 and the motion amount in the motion content, and outputs the motion control signal to the drive unit 240.

The action of Example 1 will be described. Hereinafter, control related to the insertion operation of the insertion portion 11 inserted into the intestinal tract of the large intestine from the anus will be described.

After connecting each portion of the endoscope system 1 and turning on the power, the user inserts the distal end portion 12 of the endoscope 10 into the anus of the subject. At this time, the user operates the input device 50 to set the automated insertion mode of the endoscope 10 to ON, whereby the processing device 20 executes an automated operation function of the endoscope 10.

The light source unit 210 supplies illumination light to the endoscope 10, and the imaging unit 110 images the subject irradiated with the illumination light at a predetermined cycle and transmits an imaging signal to the processing device 20. The signal processor 220 generates an endoscopic image from the imaging signal and supplies the endoscopic image to the display processor 250 and the image acquisition unit 261.

The coil drive signal generator 230 supplies coil drive signals to the plurality of source coils 18, the reception antenna 310 detects the magnetic field generated by each of the plurality of source coils 18, and the insertion shape information acquisition unit 320 generates insertion shape information of the insertion portion 11. The insertion shape information is supplied to the controller 260 and the external force information acquisition device 40. The external force information acquisition device 40 generates external force information at the position of each of the plurality of source coils 18 from the insertion shape information, and supplies the external force information to the controller 260.

The segmentation unit 262 partitions the endoscopic image acquired by the image acquisition unit 261 into a plurality of regions and generates region information of the endoscopic image. The depth information generator 263 generates information indicating the depth of the endoscopic image acquired by the image acquisition unit 261. The recognition unit 264 receives the region information of the endoscopic image from the segmentation unit 262, receives the depth information of the endoscopic image from the depth information generator 263, and recognizes the situations around the distal end portion of the endoscope. The recognition unit 264 recognizes the structure such as the lumen direction and the fold included in the endoscopic image together with the positional relationship in the depth direction using the region information of the endoscopic image and the depth information of the endoscopic image.

The motion determiner 265 generates information on the advancing direction of the endoscope based on the situations around the distal end portion of the endoscope recognized by the recognition unit 264. Specifically, the motion determiner 265 generates information on the advancing direction of the endoscope based on the direction in which the distal end portion of the endoscope can be advanced and the direction in which the distal end portion of the endoscope should not be advanced, which directions are recognized by the recognition unit 264, and determines the motion content of the distal end portion of the endoscope.

The motion controller 266 generates a motion control signal that controls the motion of the endoscope 10 based on the motion content determined by the motion determiner 265. At this time, the motion controller 266 may perform processing for setting the motion amount in the determined motion content based on at least one of the insertion shape information output from the insertion shape detection device 30 and the external force information output from the external force information acquisition device 40. The motion controller 266 generates a motion control signal corresponding to the determined motion content and the set motion amount, and outputs the motion control signal to the drive unit 240.

The motion controller 266 generates a motion control signal that controls the motion of the endoscope 10 based on an operation content determined by the motion determiner 265. At this time, the motion controller 266 may perform processing for setting the motion amount in the determined operation content based on at least one of the insertion shape information output from the insertion shape detection device 30 and the external force information output from the external force information acquisition device 40. The motion controller 266 generates a motion control signal for performing motion control in accordance with the determined operation content and the set motion amount, and outputs the motion control signal to the drive unit 240.

In a case where the motion content determined by the motion determiner 265 is an angle operation, the motion controller 266 sets a bending angle CDS of the bent portion 13 as the motion amount in the operation content. Then, the motion controller 266 generates a motion control signal that executes control to bend the bent portion 13 by the bending angle CDS, and outputs the motion control signal to the drive unit 240.

In a case where the motion content determined by the motion determiner 265 is an advance operation, the motion controller 266 sets a movement amount MES of the insertion portion 11 as the motion amount in the operation content. Then, the motion controller 266 generates a motion control signal that executes control to advance the insertion portion 11 by the movement amount MES, and outputs the motion control signal to the drive unit 240. Note that the movement amount MES is preferably set as a value within a range in which the insertion portion 11 inserted into the intestinal tract can be safely advanced.

In a case where the motion content determined by the motion determiner 265 is a retraction operation, the motion controller 266 sets a movement amount MFS of the insertion portion 11 as the motion amount in the operation content. Then, the motion controller 266 generates a motion control signal that executes control to retract the insertion portion 11 by the movement amount MFS, and outputs the motion control signal to the drive unit 240. Note that the movement amount MFS is preferably set as a value within a range in which the insertion portion 11 inserted into the intestinal tract can be safely retracted.

In a case where the operation content determined by the motion determiner 265 is a search operation, the motion controller 266 sets a movement amount MGS of the insertion portion 11 as the motion amount in the operation content. Then, the motion controller 266 generates a motion control signal that executes control to retract the insertion portion 11 by the movement amount MGS and then direct the distal end portion 12 in a plurality of directions, and outputs the motion control signal to the drive unit 240. At this time, the motion controller 266 may generate a motion control signal that executes control to direct the distal end portion 12 in four or eight directions. In the processing related to a search operation SES, processing of directing the distal end portion 12 in a plurality of directions and finding a normal lumen from the endoscopic images photographed in each of the directions is performed.

The motion controller 266 sets the motion amount based on at least one of the insertion shape information output from the insertion shape detection device 30 and the external force information output from the external force information acquisition device 40, but may set the motion amount by reading a setting value stored in advance in the storage medium 24.

Example 2

Figure 19:
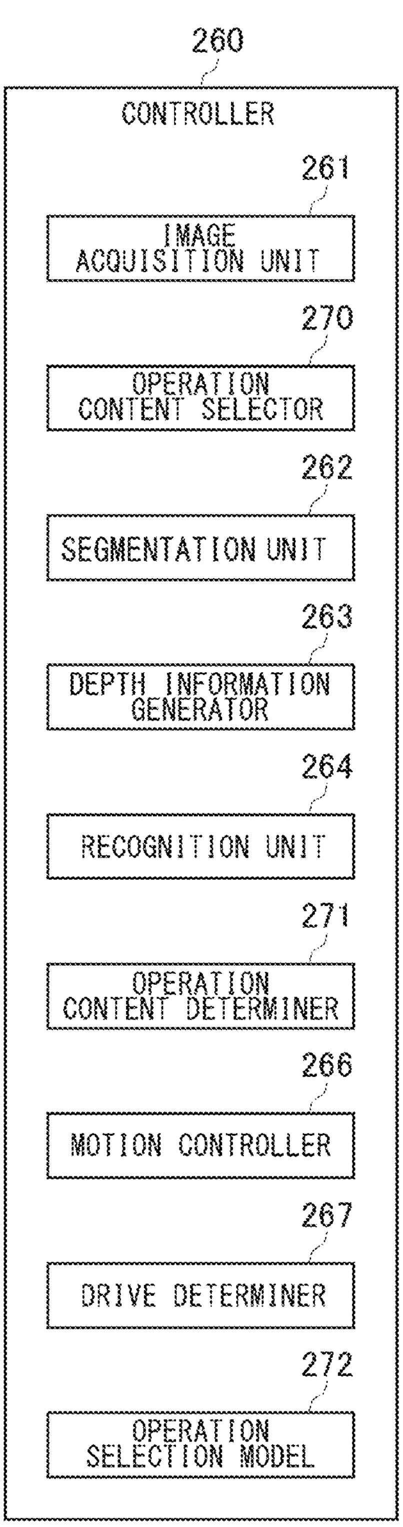
FIG. 19 is a diagram illustrating functional blocks of a controller according to Example 2.

FIG. 19 illustrates functional blocks of the controller 260 in Example 2. The controller 260 includes an image acquisition unit 261, an operation content selector 270, a segmentation unit 262, a depth information generator 263, a recognition unit 264, an operation content determiner 271, a motion controller 266, a drive determiner 267, and an operation selection model 272.

The controller 260 shown in FIG. 19 includes a computer or is a function of a computer, and various functions shown in FIG. 19 are implemented by the computer executing programs. The computer includes, as hardware, a memory for loading programs, one or more processors 22 for executing the loaded programs, an auxiliary storage device, other LSIs, and the like. The processor is composed of a plurality of electronic circuits including a semiconductor integrated circuit and an LSI, and the plurality of electronic circuits may be mounted on one chip or may be mounted on a plurality of chips. It should be understood by those skilled in the art that the functional blocks shown in FIG. 19 are implemented by cooperation of hardware and software, and thus, these functional blocks can be implemented in various forms by hardware alone, or software alone, or a combination thereof. For example, a program for executing at least some functions of the controller 260 may be stored in the storage medium 24, and the processor 22 may load the program from the storage medium 24 into a memory to implement each function of the controller 260.

The image acquisition unit 261, the segmentation unit 262, the depth information generator 263, the recognition unit 264, the motion controller 266, and the drive determiner 267 in Example 2 have the same or similar functions as those of the image acquisition unit 261, the segmentation unit 262, the depth information generator 263, the recognition unit 264, the motion controller 266, and the drive determiner 267 described in Example 1, and thus redundant descriptions will be appropriately omitted below.

The image acquisition unit 261 acquires an endoscopic image photographed by the endoscope 10 being inserted into the subject from the signal processor 220. In Example 2, the image acquisition unit 261 supplies the acquired endoscopic image to the operation content selector 270, the segmentation unit 262, and the depth information generator 263.

The operation content selector 270 has a function of selecting one or more operation contents from a plurality of predetermined operation contents based on the endoscopic image acquired by the image acquisition unit 261. In other words, the operation content selector 270 selects the operation content to be performed from a plurality of options of endoscope operation based on the endoscopic image obtained by photographing the inside of the subject. The plurality of predetermined operation contents may include at least one type of operation of an advance operation, a retraction operation, an angle operation, a twist operation, an air supply operation, a water supply operation, and a suction operation.

The operation content selector 270 inputs input data acquired from the endoscopic image acquired by the image acquisition unit 261 to the operation selection model 272, thereby selecting operation content recommended for the endoscope 10 that is photographing the endoscopic image. The operation selection model 272 is a learned model generated by machine learning using a learning image that is an endoscopic image photographed in the past and a label indicating an operation content for the endoscope that has photographed the learning image as supervised data.

In Example 2, the operation selection model 272 is generated by learning each coupling coefficient (weight) in a convolutional neural network (CNN) corresponding to a multilayer neural network that includes an input layer, one or more convolution layers, and an output layer by a learning method such as deep learning.

The segmentation unit 262 has a function of partitioning the endoscopic image acquired by the image acquisition unit 261 into a plurality of regions. Specifically, the segmentation unit 262 executes semantic segmentation that labels each pixel in the endoscopic image to partition the endoscopic image into regions of each structure. The segmentation unit 262 defines a region having a structure of a type (a class) to be partitioned, and generates a segmentation result obtained by labeling pixels of various structures. The segmentation unit 262 supplies the region information indicating the result of the segmentation to the recognition unit 264.

The depth information generator 263 has a function of generating information indicating the depth of the endoscopic image acquired by the image acquisition unit 261. Conventionally, various methods for estimating the depth of a pixel or a block included in an image have been proposed. The depth information generator 263 may generate information indicating the depth of each pixel of the endoscopic image using, for example, the technique disclosed in Non Patent Literature 2. The depth information generator 263 supplies the depth information of the endoscopic image to the recognition unit 264.

The recognition unit 264 recognizes the situation around the distal end portion of the endoscope based on the region information indicating the result of the segmentation by the segmentation unit 262 and/or the depth information of the endoscopic image generated by the depth information generator 263. Specifically, the recognition unit 264 specifies at least the direction in which the endoscope 10 can be advanced and the direction in which the endoscope 10 should not be advanced as the situation around the distal end portion of the endoscope.

The operation content determiner 271 determines the operation content to be performed based on the operation content selected in the operation content selector 270 and the situation around the distal end portion of the endoscope recognized by the recognition unit 264.

In Example 2, the operation content determiner 271 may determine the operation content of the endoscope 10 at each timing at which the image acquisition unit 261 acquires an endoscopic image, and the motion controller 266 may generate a motion control signal in accordance with the determined operation content and supply the motion control signal to the drive unit 240. Note that, as another timing example, the drive unit 240 may drive the motion mechanism of the endoscope 10 based on the motion control signal by the motion controller 266, at the timing when the drive is ended, the operation content determiner 271 may determine the operation content of the endoscope 10, and the motion controller 266 may generate the motion control signal.

Operation Content Selection Processing

In generating the operation selection model 272, machine learning is performed using supervised data that includes a learning image that is an endoscopic image obtained by photographing the inside of the intestinal tract or a colonoscopy phantom in the past with an endoscope and a label that indicates which of the 12 operation contents is most suitable for the situations indicated by the learning image.

Here, the 12 operation contents include the following.

- Angle operation UPS for bending the bent portion 13 and directing the distal end portion 12 in an upward direction
- Angle operation RIS for bending the bent portion 13 and directing the distal end portion 12 in a right direction
- Angle operation DOS for bending the bent portion 13 and directing the distal end portion 12 in a downward direction
- Angle operation LES for bending the bent portion 13 and directing the distal end portion 12 in a left direction
- Angle operation URS for bending the bent portion 13 and directing the distal end portion 12 in an upward right direction
- Angle operation DRS for bending the bent portion 13 and directing the distal end portion 12 in a downward right direction
- Angle operation DLS for bending the bent portion 13 and directing the distal end portion 12 in a downward left direction
- Angle operation ULS for bending the bent portion 13 and directing the distal end portion 12 in an upward left direction
- Advance operation PSS for advancing the distal end portion 12
- Retraction operation PLS for retracting the distal end portion 12
- Search operation SES for searching for a lumen by directing the distal end portion 12 in a plurality of directions
- Angle maintenance operation AMS for fixing the bending angle of the bent portion 13 and maintaining an orientation of distal end portion 12 at the current orientation During creation of the supervised data, an expert views the learning image, subjectively selects one operation content that can be performed most in the situations shown in the learning image from the 12 operation contents described above, and assigns a label of the selected operation content to the learning image. The expert may be a physician. For example, in a case where the endoscopic image 70*b* shown in FIG. 3(*b*) is a learning image, since the lumen center exists in the upper portion of the image, the expert determines that the operation of directing the distal end portion of the endoscope in the upward direction, that is, the angle operation UPS should be performed, and assigns a label of the angle operation UPS to the endoscopic image 70*b*. Performing this labeling work on a large number of past endoscopic images creates supervised data.

Hereinafter, an example of supervised data that includes a learning image and a label will be described.

Figure 20:
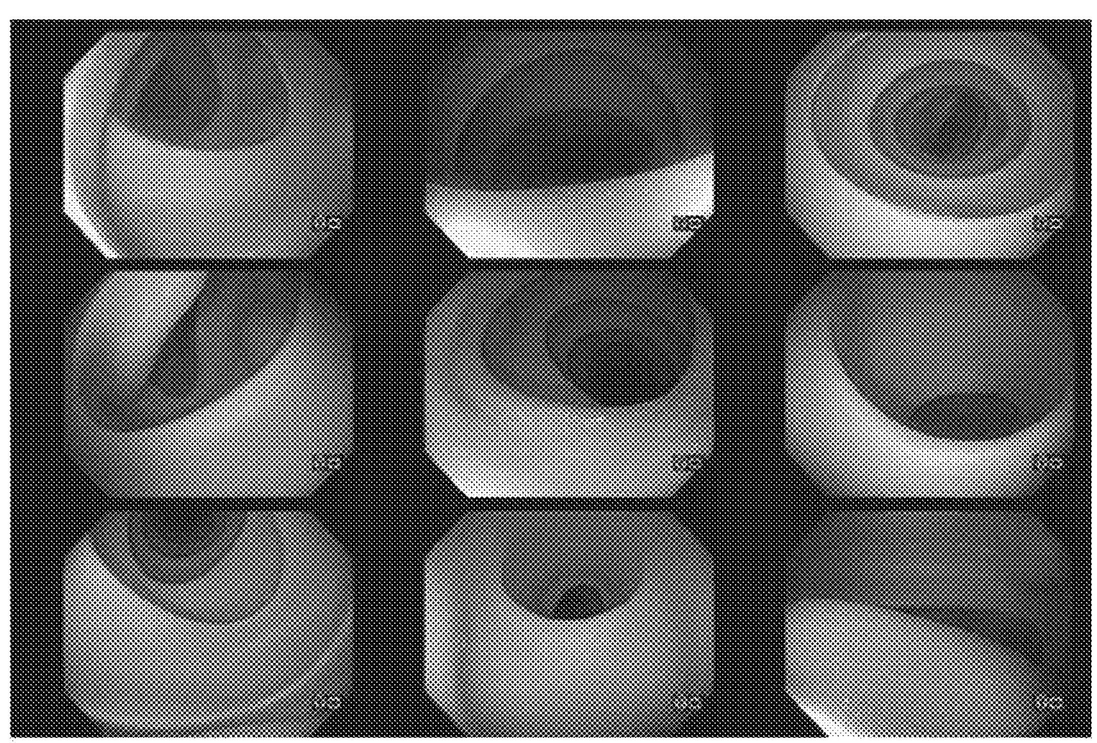
FIG. 20 is a view illustrating an example of supervised data.

FIG. 20 illustrates an example of supervised data. A "label of angle operation UPS" indicating the angle operation in the upward direction is assigned to each of the learning images shown in FIG. 20. The learning image shown in FIG. 20 is an image in which it is determined that the bent portion 13 should be bent in the upward direction as the endoscope operation to be performed.

Figure 21:
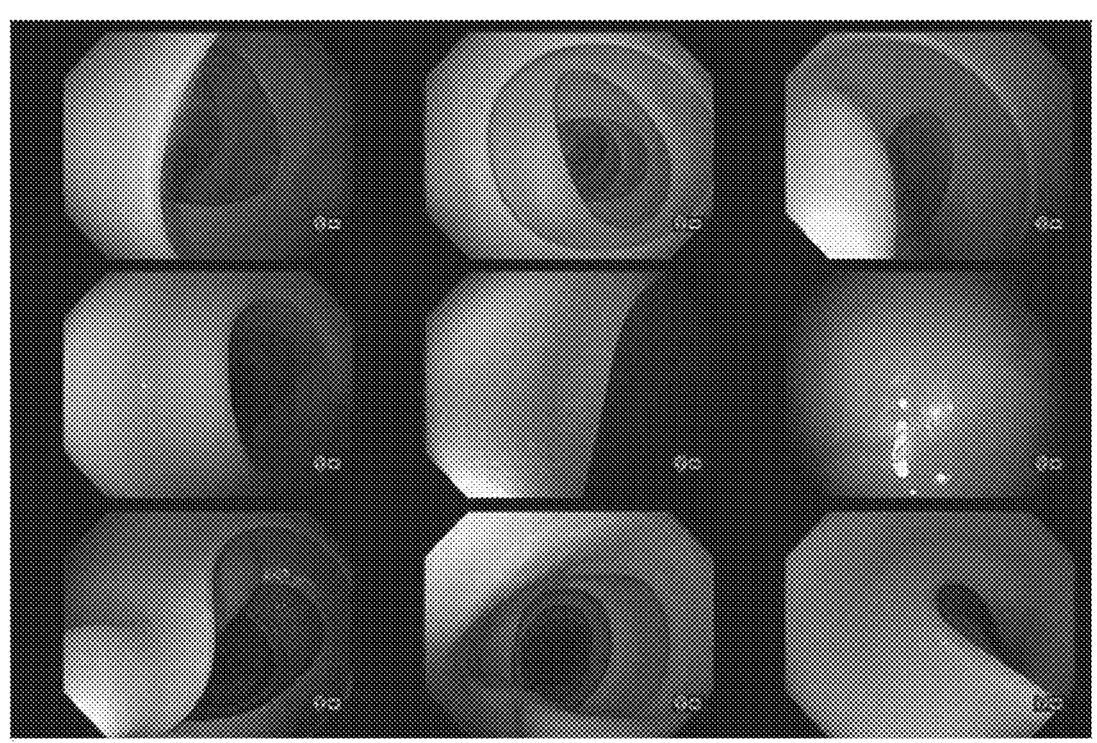
FIG. 21 is a view illustrating another example of supervised data.

FIG. 21 illustrates another example of supervised data. A "label of angle operation RIS" indicating the angle operation in the right direction is assigned to each of the learning images shown in FIG. 21. The learning image shown in FIG. 21 is an image in which it is determined that the bent portion 13 should be bent in the right direction as the endoscope operation to be performed.

Figure 22:
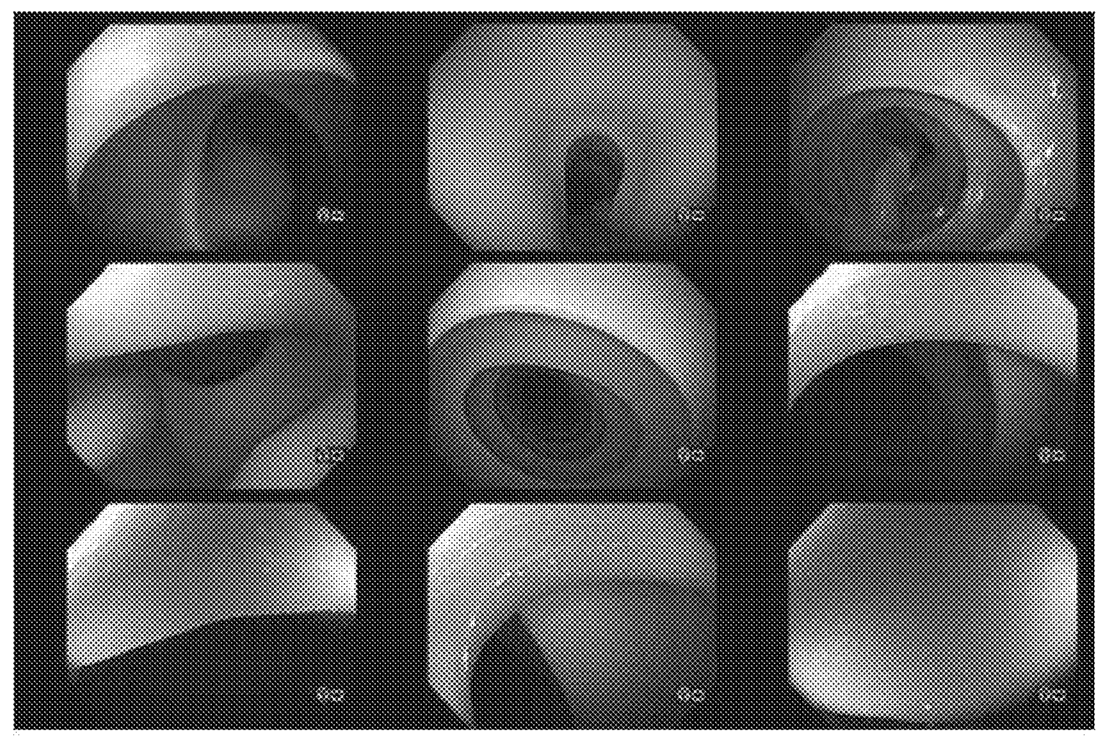
FIG. 22 is a view illustrating another example of supervised data.

FIG. 22 illustrates another example of supervised data. A "label of angle operation DOS" indicating the angle operation in the downward direction is assigned to each of the learning images shown in FIG. 22. The learning image shown in FIG. 22 is an image in which it is determined that the bent portion 13 should be bent in the downward direction as the endoscope operation to be performed.

Figure 23:
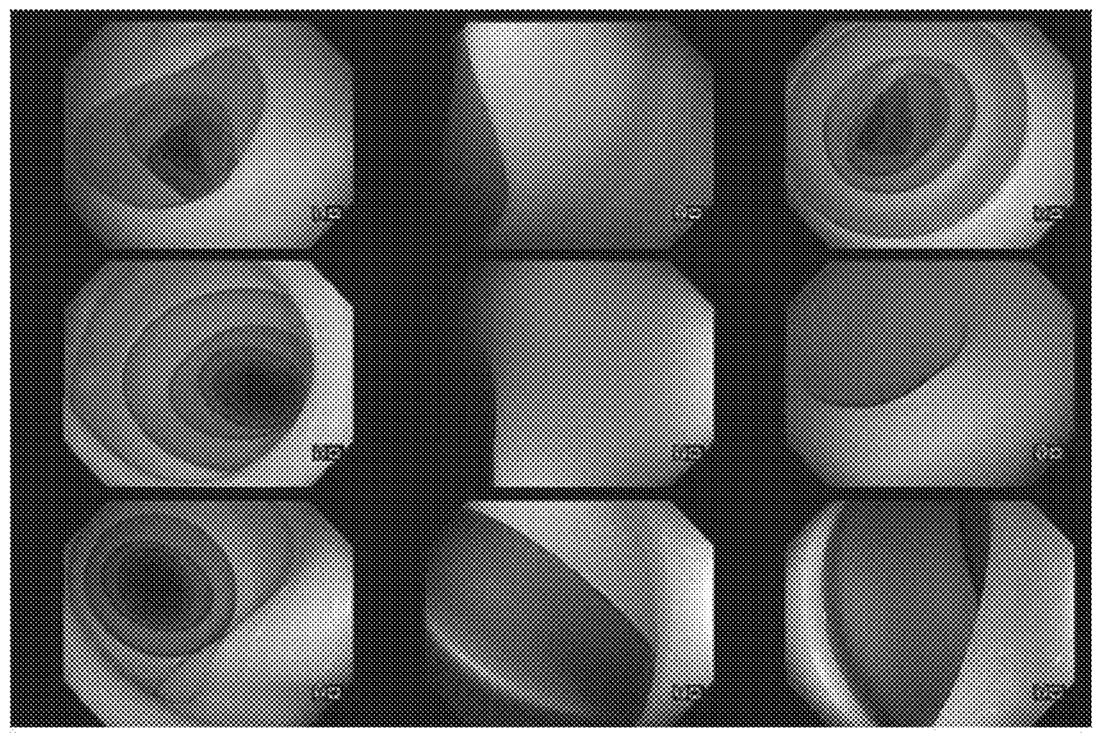
FIG. 23 is a view illustrating another example of supervised data.

FIG. 23 illustrates another example of supervised data. A "label of angle operation LES" indicating the angle operation in the left direction is assigned to each of the learning images shown in FIG. 23. The learning image shown in FIG. 23 is an image in which it is determined that the bent portion 13 should be bent in the left direction as the endoscope operation to be performed.

Figure 24:
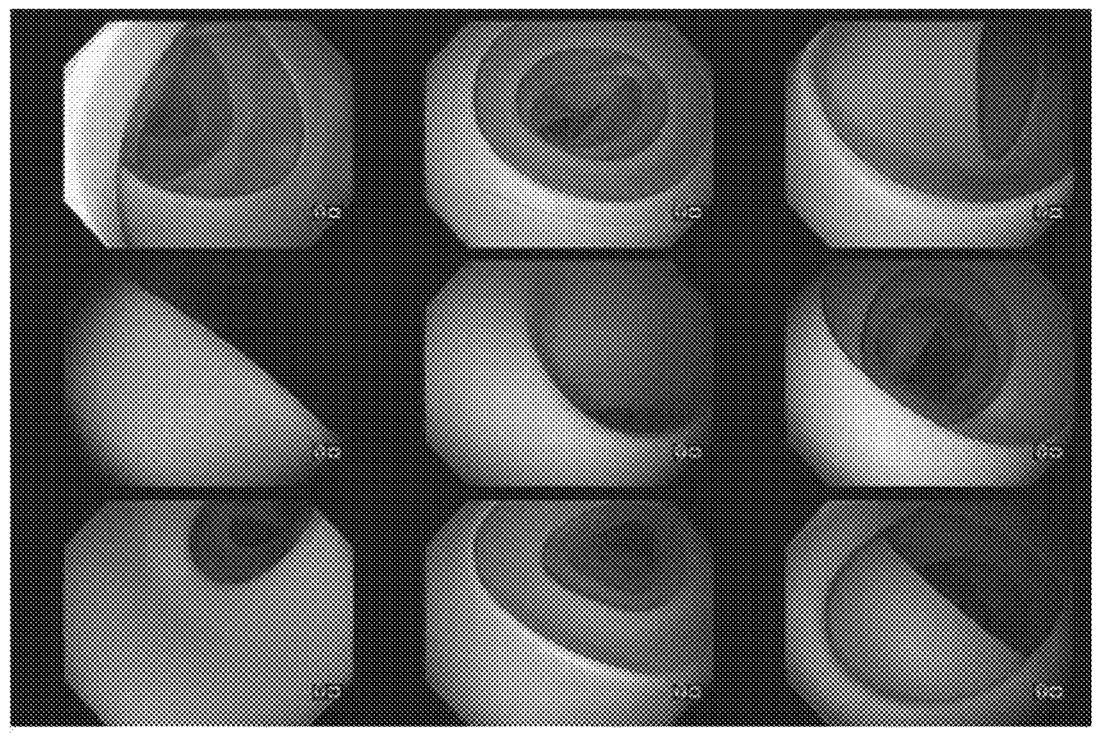
FIG. 24 is a view illustrating another example of supervised data.

FIG. 24 illustrates another example of supervised data. A "label of angle operation URS" indicating the angle operation in the upward right direction is assigned to each of the learning images shown in FIG. 24. The learning image shown in FIG. 24 is an image in which it is determined that the bent portion 13 should be bent in the upward right direction as the endoscope operation to be performed.

Figure 25:
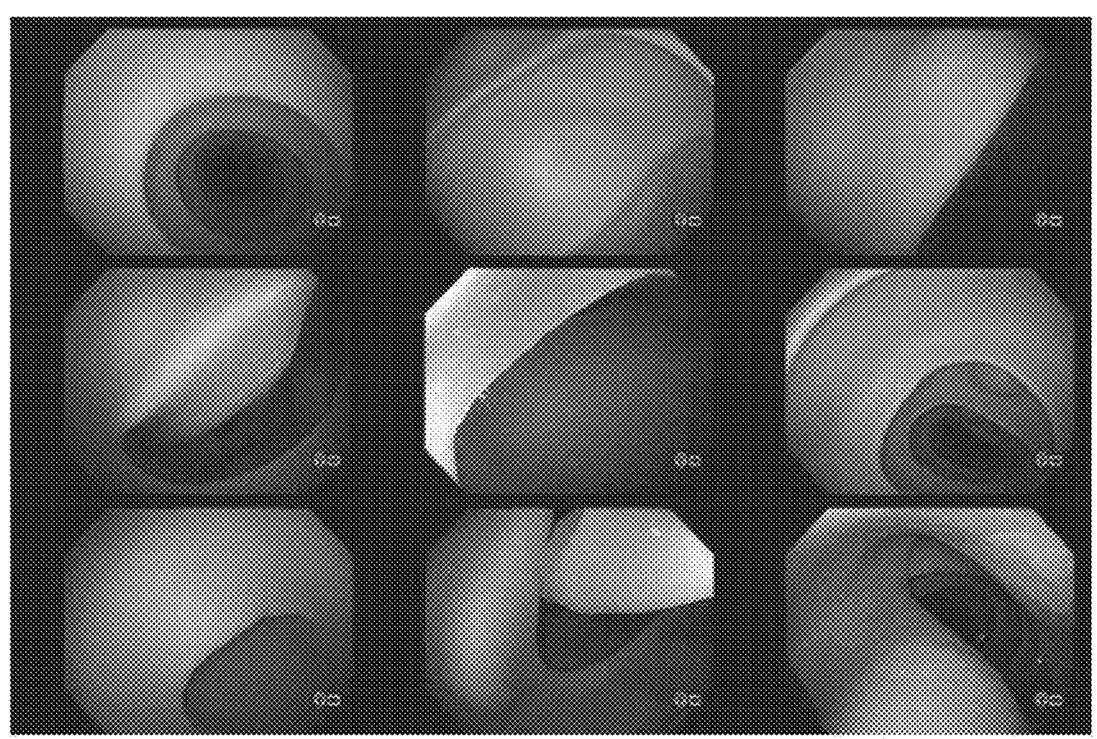
FIG. 25 is a view illustrating another example of supervised data.

FIG. 25 illustrates another example of supervised data. A "label of angle operation DRS" indicating the angle operation in the downward right direction is assigned to each of the learning images shown in FIG. 25. The learning image shown in FIG. 25 is an image in which it is determined that the bent portion 13 should be bent in the downward right direction as the endoscope operation to be performed.

Figure 26:
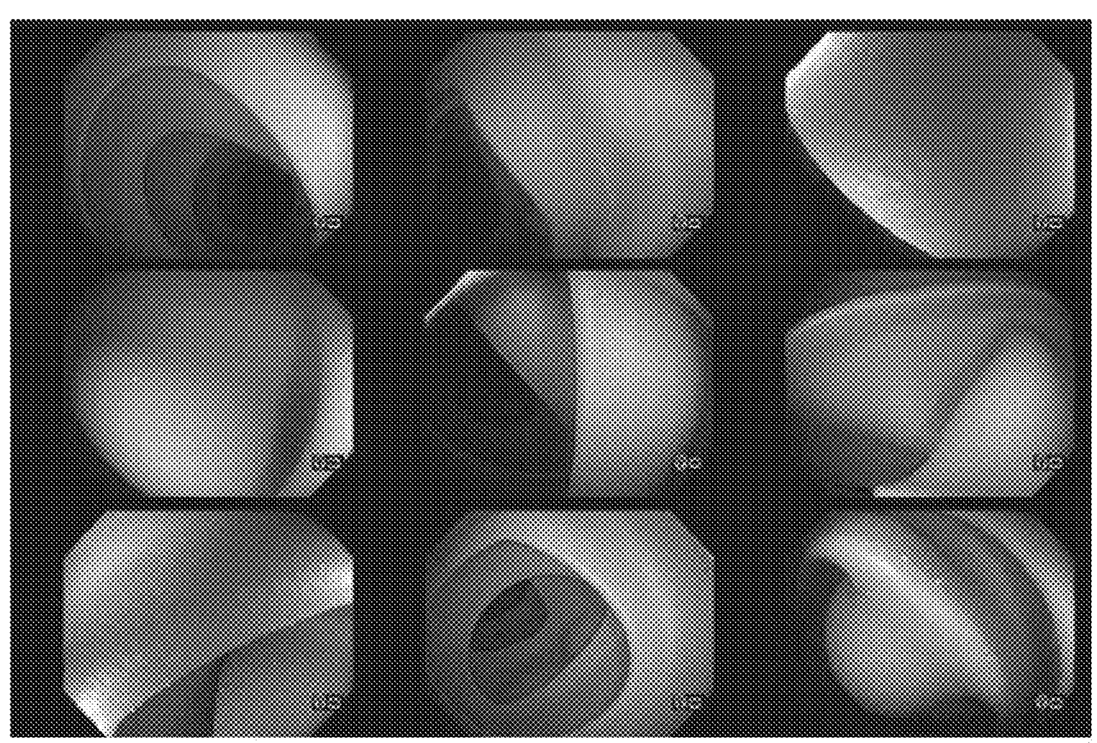
FIG. 26 is a view illustrating another example of supervised data.

FIG. 26 illustrates another example of supervised data. A "label of angle operation DLS" indicating the angle operation in the downward left direction is assigned to each of the learning images shown in FIG. 26. The learning image shown in FIG. 26 is an image in which it is determined that the bent portion 13 should be bent in the downward left direction as the endoscope operation to be performed.

Figure 27:
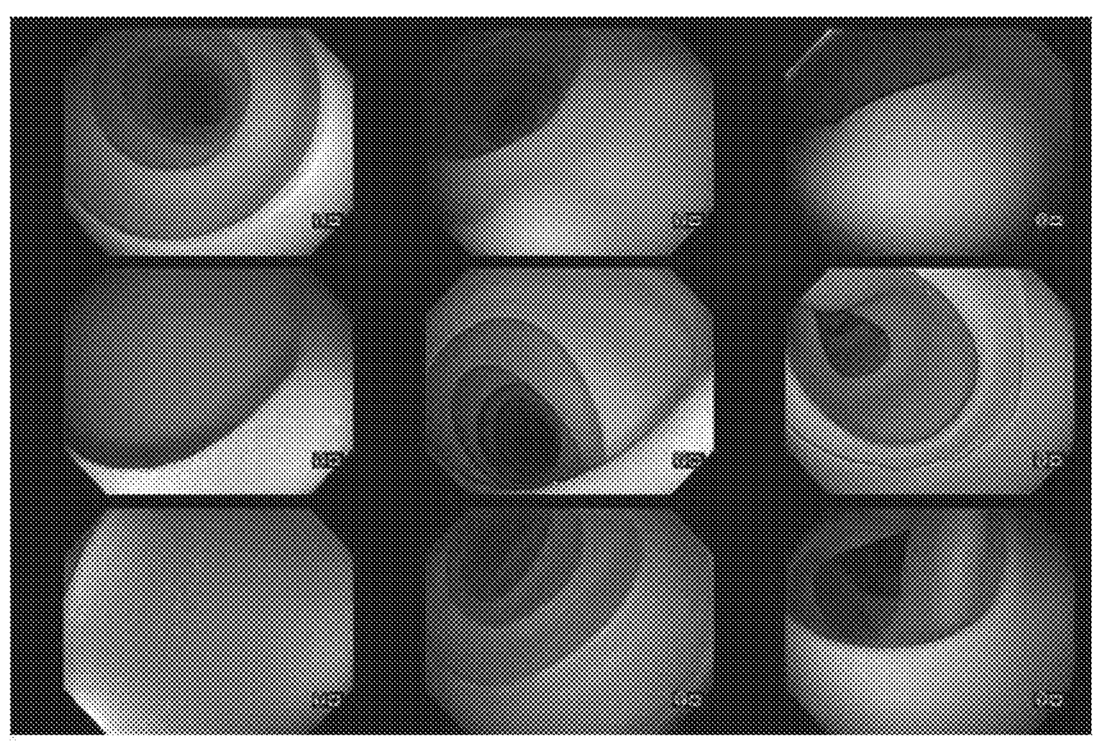
FIG. 27 is a view illustrating another example of supervised data.

FIG. 27 illustrates another example of supervised data. A "label of angle operation ULS" indicating the angle operation in the upward left direction is assigned to each of the learning images shown in FIG. 27. The learning image shown in FIG. 27 is an image in which it is determined that the bent portion 13 should be bent in the upward left direction as the endoscope operation to be performed.

Figure 28:
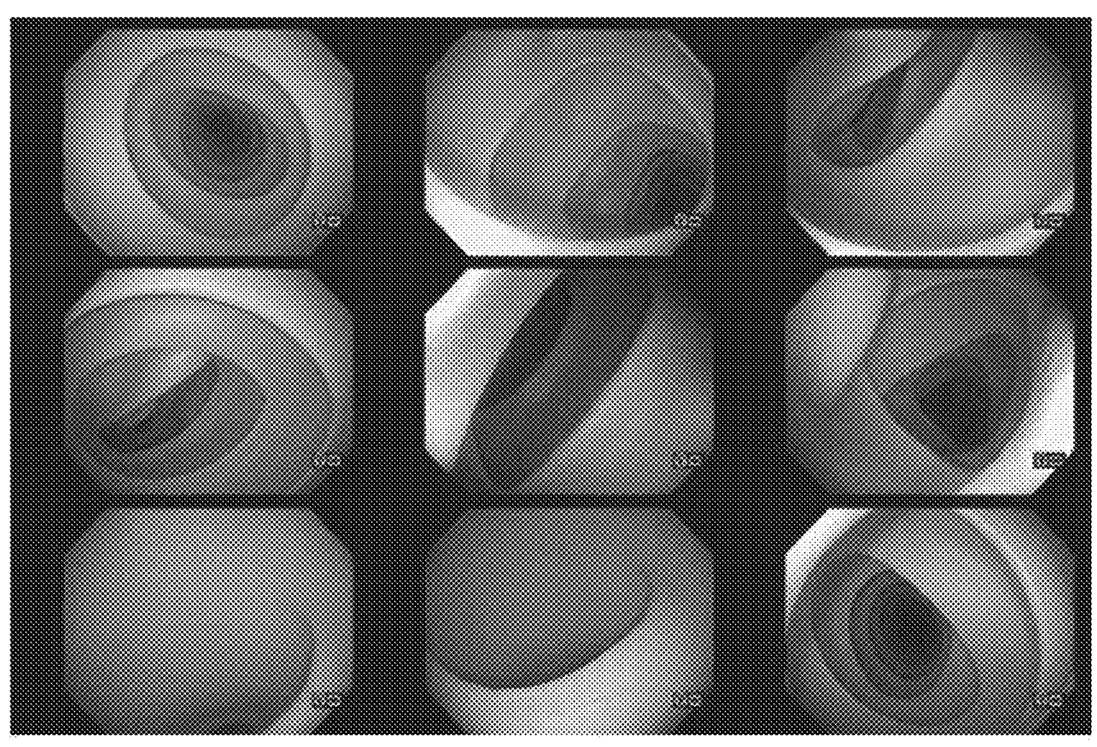
FIG. 28 is a view illustrating another example of supervised data.

FIG. 28 illustrates another example of supervised data. A "label of pushing operation (advance operation) PSS" indicating the advance operation is assigned to each of the learning images shown in FIG. 28. The learning image shown in FIG. 28 is an image in which it is determined that the distal end portion 12 should be advanced as the endoscope operation to be performed.

Figure 29:
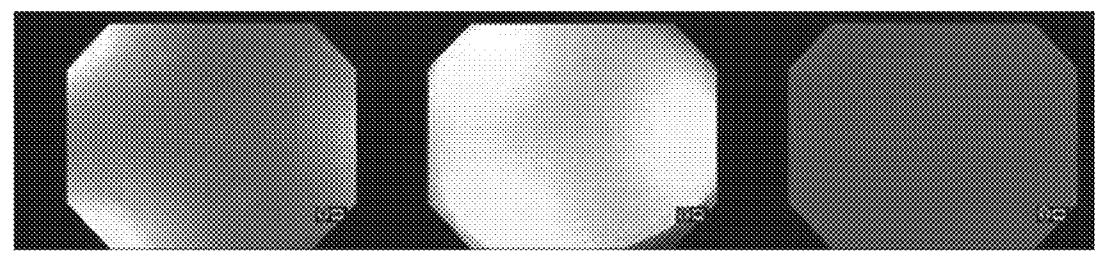
FIG. 29 is a view illustrating another example of supervised data.

FIG. 29 illustrates another example of supervised data. A "label of pulling operation (retraction operation) PLS" indicating the retraction operation is assigned to each of the learning images shown in FIG. 29. The learning image shown in FIG. 29 is an image in which it is determined that the distal end portion 12 should be retracted as the endoscope operation to be performed. Here, typical examples of situations in which the retraction operation is necessary include a situation in which the distal end portion 12 is excessively close to the mucosal surface of the large intestine and a situation in which the distal end portion 12, commonly referred to as a "red ball" among endoscopists, is in contact with the mucosal surface.

Figure 30:
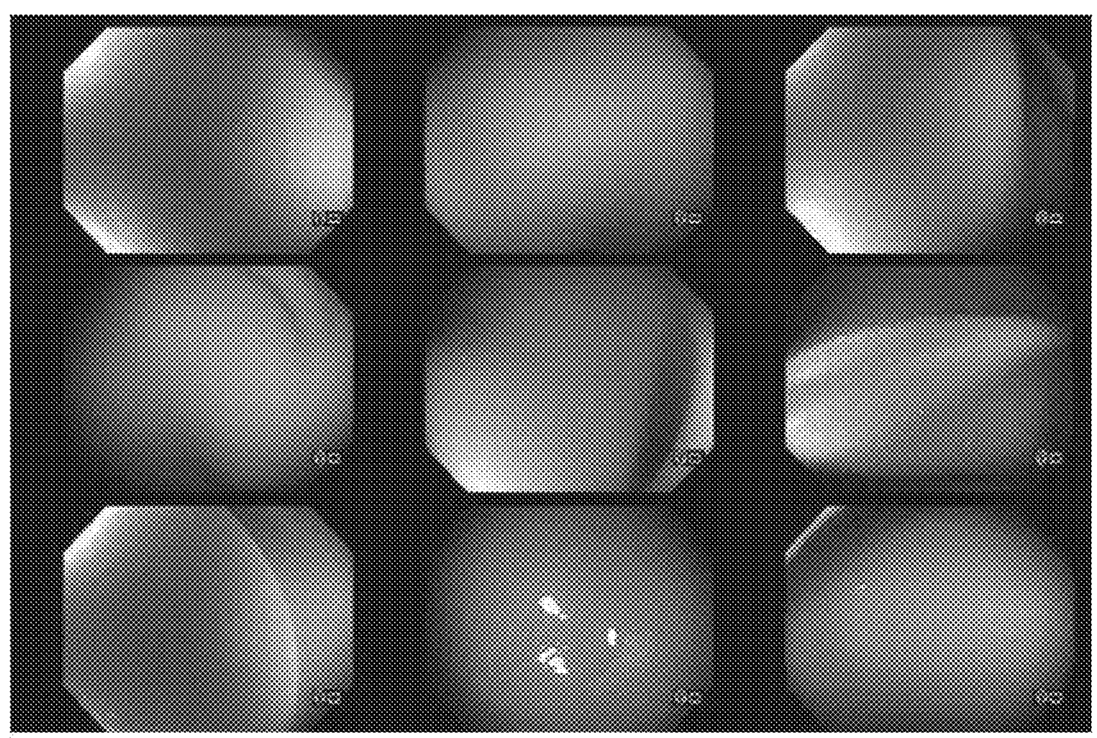
FIG. 30 is a view illustrating another example of supervised data.

FIG. 30 illustrates another example of supervised data. A "label of search operation SES" indicating the search operation is assigned to each of the learning images shown in FIG. 30. The learning image shown in FIG. 30 is an image in which it is determined that the bent portion 13 should be bent in multiple directions and photographed in a plurality of directions as the endoscope operation to be performed.

Although illustration of the supervised data of the angle maintenance operation AMS for fixing the bending angle of the bent portion 13 and maintaining the orientation of the distal end portion 12 at the current orientation is omitted, for example, a label of "angle maintenance operation AMS" may be assigned to the learning image shown in FIG. 28.

The operation selection model 272 of Example 2 is generated by machine learning using the supervised data shown in FIGS. 20 to 30.

The operation content selector 270 selects one or more operation contents by inputting the input data acquired from the endoscopic image acquired in the image acquisition unit 261 to one or more operation selection models 272 generated by machine learning using the learning image and the label that indicates the operation content for the endoscope obtained by photographing the learning image as supervised data. Specifically, the operation content selector 270 acquires multidimensional data such as a pixel value of each pixel included in the endoscopic image acquired in the image acquisition unit 261, and inputs the multidimensional data to the input layer of the neural network of the operation selection model 272 as input data. The operation selection model 272 outputs, from the output layer of the neural network, 12 likelihoods respectively corresponding to the 12 operation contents that can be selected as operation contents of the endoscope 10. The operation content selector 270 can obtain the operation content corresponding to the highest likelihood among the 12 likelihoods included in the output data as a selection result of the operation content of the endoscope 10.

As described above, the operation content selector 270 is configured to input the input data acquired from the endoscopic image acquired in the image acquisition unit 261 to the operation selection model 272 and process the input data to obtain the selection result that indicates one operation content selected from the 12 operation contents that include an operation for directing the orientation of the distal end portion 12 in eight directions orthogonal to the insertion axis of the insertion portion 11, an operation for advancing or retracting the distal end portion 12, an operation for maintaining the orientation of the distal end portion 12 at the current orientation, and an operation for searching for the lumen near the distal end portion 12. The operation content selector 270 supplies the selected operation content to the operation content determiner 271.

The operation selection model 272 is preferably constructed by sufficient learning so that appropriate operation content can be output, but its accuracy depends on supervised data. Therefore, in Example 2, a method of determining whether or not the operation content selected by the operation content selector 270 is appropriate based on the situations around the distal end portion of the endoscope recognized by the recognition unit 264 is realized.

Segmentation Processing of Endoscopic Image

In parallel with the processing in the operation content selector 270, the segmentation unit 262 partitions the endoscopic image acquired by the image acquisition unit 261 into a plurality of regions. As described in Example 1, the segmentation unit 262 executes semantic segmentation of labeling each pixel in the endoscopic image to partition the endoscopic image into regions of each structure. The segmentation unit 262 may execute semantic segmentation using the FCN.

Figure 31B:
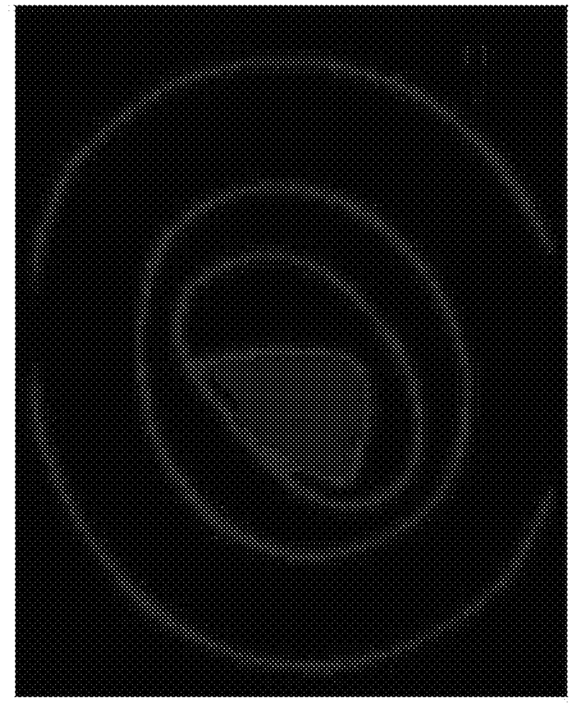
FIG. 31(*a*) is a view illustrating an example of an endoscopic image, and FIG. 31(*b*) is a view illustrating an example of a segmentation result image.
Figure 31A:

FIG. 31(*a*) illustrates an example of an endoscopic image. When acquiring an endoscopic image photographed by the endoscope 10 from the signal processor 220, the image acquisition unit 261 supplies the endoscopic image to the operation content selector 270 and the segmentation unit 262. It is assumed that, as a result of inputting the input data acquired from the endoscopic image of FIG. 31(*a*) to the operation selection model 272, the operation content selector 270 selects the "advance operation PSS" of advancing the distal end portion 12 as the operation content. The operation content selector 270 supplies the selected operation content to the operation content determiner 271.

The segmentation unit 262 executes semantic segmentation to partition the endoscopic image into a plurality of regions.

FIG. 31(*b*) illustrates an example of a segmentation result by the segmentation unit 262. The segmentation unit 262 partitions the endoscopic image into a plurality of regions and derives region information indicating a result of segmentation. Here, the region information may be derived as a label value pa(x,y) of each pixel related to the structure. The segmentation unit 262 generates a segmentation result image using the derived label value. In Example 2, the endoscopic image has a size of 720×480, and the segmentation result image also has a size of 720×480. The segmentation unit 262 supplies the segmentation result image to the recognition unit 264 as the region information indicating the result of the segmentation. The segmentation result image includes a region of fold edges having a concentric shape and a region of a normal lumen. Note that, in another example, the segmentation unit 262 may supply the label value of each pixel to the recognition unit 264 as the region information indicating the result of the segmentation.

The recognition unit 264 divides the segmentation result image having a size of 720×480 into a plurality of partial regions, and recognizes a proportion of the normal lumen region included in each partial region. In Example 2, the endoscopic image is divided into 5 equal parts in the horizontal direction and the vertical direction to be divided into 5×5 partial regions, and each partial region is expressed by sub (i,j). Note that i, j=1, 2, 3, 4, 5. In another example, the recognition unit 264 may divide the segmentation result image by a division number other than 5×5.

Figure 32:
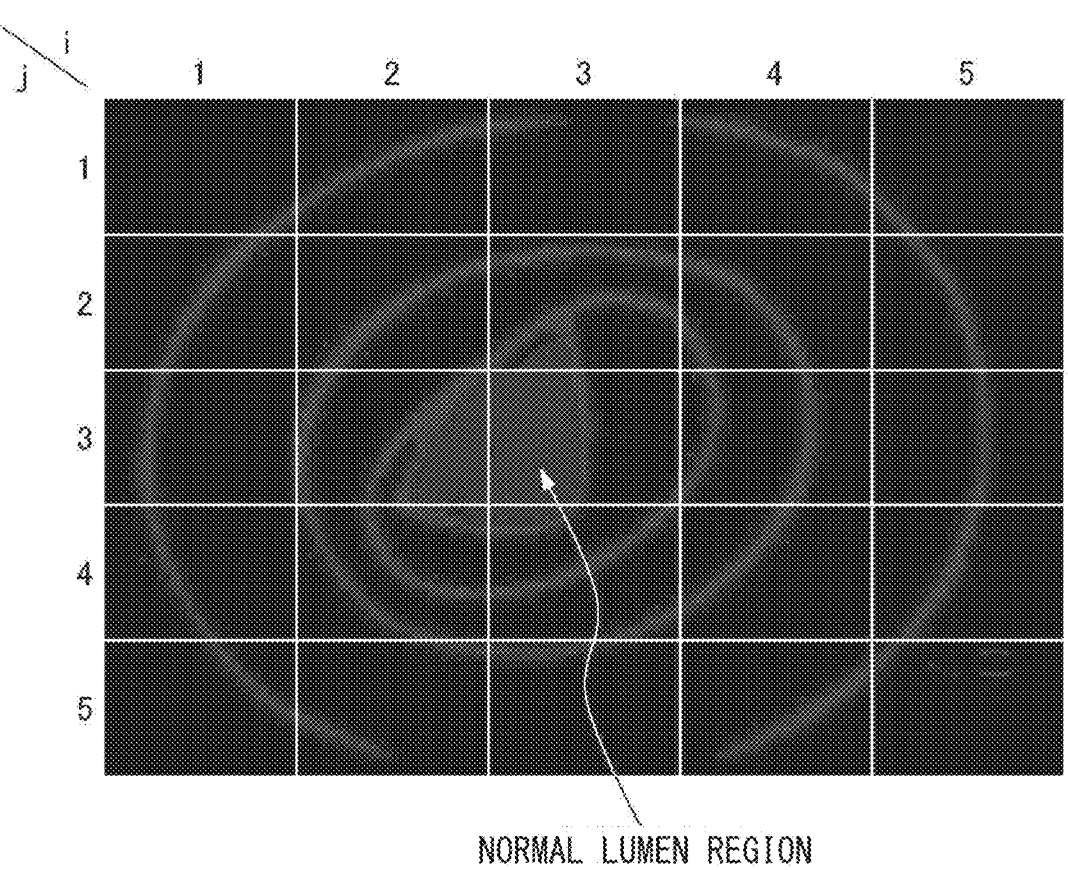
FIG. 32 is a diagram illustrating a state in which the segmentation result image is divided into a plurality of partial regions.

FIG. 32 illustrates a state in which the segmentation result image is divided into a plurality of partial regions. In this example, the region extracted as the normal lumen exists across the partial regions sub (3,2), sub (2,3), sub (3,3), sub (2,4), and sub (3,4). The recognition unit 264 derives a proportion of the number of pixels in the normal lumen in each partial region sub (i,j). This proportion is calculated by the following equation. Here, the total number of pixels of the partial region is expressed as an, and an=144×96 in this example.

Normal lumen proportion (*a*)=(number of pixels in normal lumen region in partial region)/*an*

The recognition unit 264 may determine the normal lumen region included in the partial region where the proportion (a) exceeds a predetermined threshold value (for example, 0.4) as a region where the endoscope can be advanced. In this example, the normal lumen proportion (a) calculated for sub (3,3) exceeds the threshold value, and thus the recognition unit 264 recognizes that a region where the endoscope can be advanced exists in sub (3,3) in the endoscopic image. The recognition unit 264 recognizes a direction in which the endoscope can be advanced by specifying a region where the endoscope can be advanced. The recognition unit 264 supplies the recognition result to the operation content determiner 271.

Note that, in the above example, the recognition unit 264 determines the region where the endoscope can be advanced from the proportion of the number of pixels in the normal lumen in each partial region sub (i,j) In another example, the recognition unit 264 may recognize a partial region sub (i,j) that includes a predetermined proportion or more of the total number of pixels in the normal lumen as a partial region where the endoscope can be advanced. In this case, the recognition unit 264 counts the number of pixels pl divided into regions as a normal lumen. The recognition unit 264 derives a proportion of the normal lumen region included in each partial region sub (i,j) to an entire normal lumen region. This proportion is derived by the following equation.

Normal lumen proportion (*b*)=(number of pixels in normal lumen region in partial region)/*pl*

The recognition unit 264 may determine the partial region where the proportion (b) exceeds a predetermined threshold value (for example, 0.6) as a region where the endoscope can be advanced. In this example, the normal lumen proportion (b) calculated for sub (3,3) exceeds the threshold, and thus the recognition unit 264 recognizes that a region where the endoscope can be advanced exists in sub (3,3) in the endoscopic image. Note that the recognition unit 264 may specify a partial region where the proportion (b) is a maximum as a region where the endoscope can be advanced. The recognition unit 264 recognizes a direction in which the endoscope can be advanced by specifying a region where the endoscope can be advanced. The recognition unit 264 supplies the recognition result to the operation content determiner 271. The recognition unit 264 may specify a region and a direction in which the endoscope can be advanced based on either the normal lumen proportion (a) or the normal lumen proportion (b).

The operation content determiner 271 receives the operation content selected from the operation content selector 270 and receives the recognition result of the situations around the distal end portion from the recognition unit 264. The operation content determiner 271 determines whether the operation content selected by the operation content selector 270 is appropriate based on the situations recognized by the recognition unit 264. Here, the operation content determiner 271 selects the "advance operation PSS" of advancing the distal end portion 12 as the operation content, and the recognition unit 264 recognizes that a region where the distal end portion of the endoscope can be advanced exists in sub (3,3) located at the center of the endoscopic image. Since sub (3,3) exists in an advancing direction of the distal end portion of the endoscope, the operation content determiner 271 determines that the advance operation PSS selected by the operation content selector 270 is appropriate, and determines the advance operation PSS as the operation content to be performed.

Figures 33A, 33B:
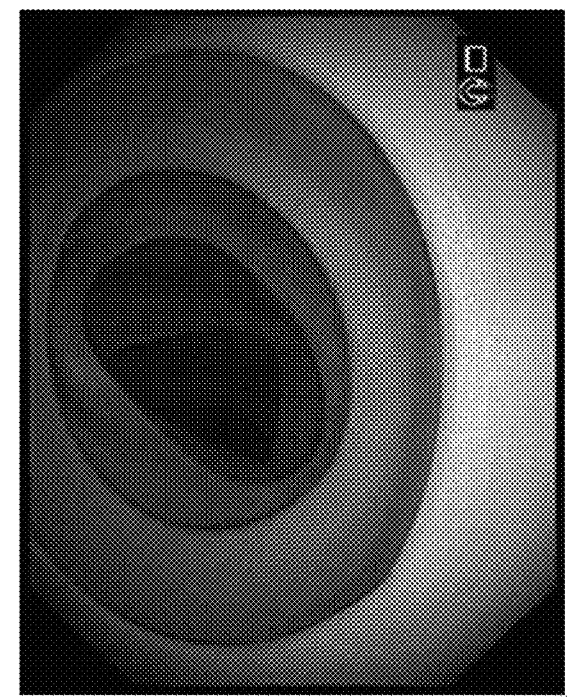
FIG. 33(*a*) is a view illustrating an example of an endoscopic image, and FIG. 33(*b*) is a view illustrating an example of a segmentation result image.

FIG. 33(*a*) illustrates another example of an endoscopic image. When acquiring an endoscopic image photographed by the endoscope 10 from the signal processor 220, the image acquisition unit 261 supplies the endoscopic image to the operation content selector 270 and the segmentation unit 262. It is assumed that, as a result of inputting the input data acquired from the endoscopic image of FIG. 33(*a*) to the operation selection model 272, the operation content selector 270 selects the "advance operation PSS" of advancing the distal end portion 12 as the operation content. The operation content selector 270 supplies the selected operation content to the operation content determiner 271.

FIG. 33(*b*) illustrates an example of a segmentation result by the segmentation unit 262. The segmentation unit 262 partitions the endoscopic image into a plurality of regions and derives region information indicating a result of segmentation. The region information is derived as a label value pa(x,y) of each pixel related to the structure, and the segmentation unit 262 generates a segmentation result image using the derived label value. The segmentation unit 262 supplies the segmentation result image to the recognition unit 264 as the region information indicating the result of the segmentation. The recognition unit 264 divides the segmentation result image into 5×5 partial regions, and recognizes the proportion of the normal lumen region included in each partial region.

Figure 34:
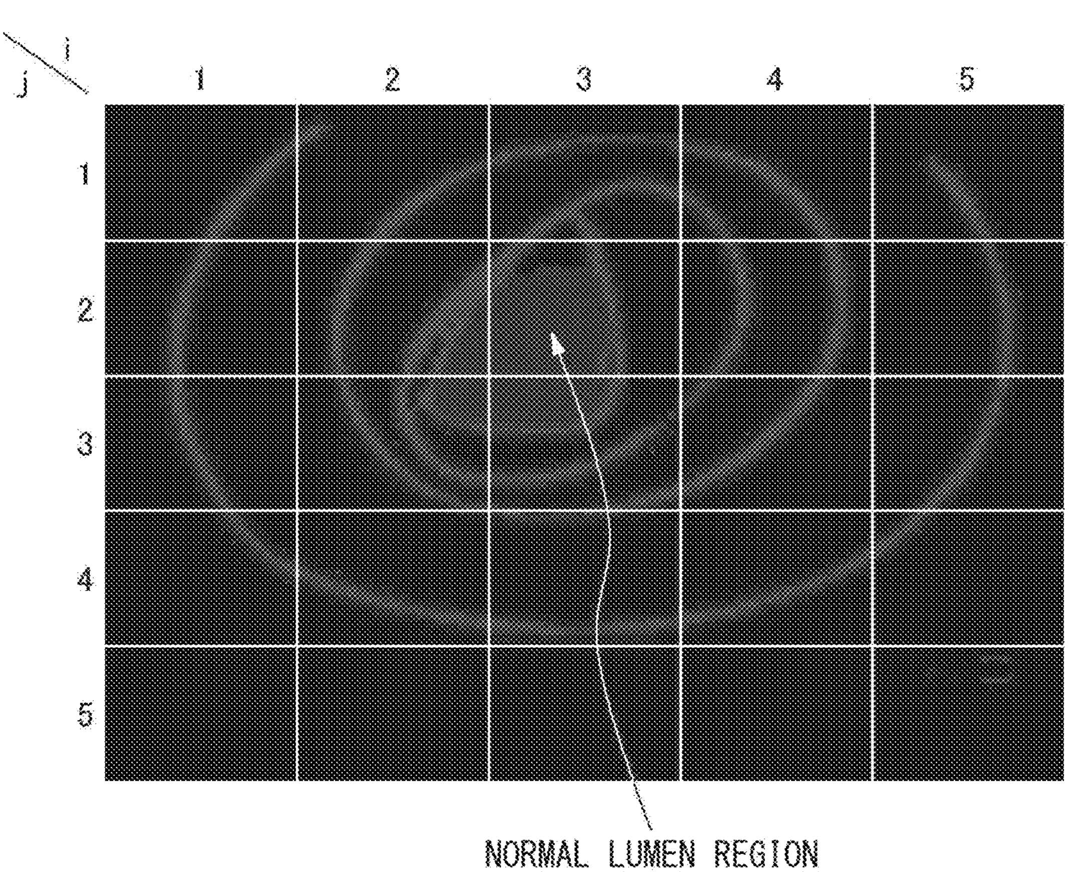
FIG. 34 is a diagram illustrating a state in which the segmentation result image is divided into a plurality of partial regions.

FIG. 34 illustrates a state in which the segmentation result image is divided into a plurality of partial regions. In this example, the region extracted as the normal lumen exists across the partial regions sub (2,2), sub (3,2), sub (2,3), and sub (3,3). The recognition unit 264 derives a proportion of the number of pixels in the normal lumen in each partial region sub (i,j). In this example, the recognition unit 264 calculates the normal lumen proportion (b), and recognizes that the normal lumen proportion (b) exceeds a predetermined threshold (for example, 0.6) in sub (3,2). Therefore, the recognition unit 264 recognizes that a region where the endoscope can be advanced exists in sub (3,2) in the endoscopic image. The recognition unit 264 supplies the recognition result to the operation content determiner 271.

The operation content determiner 271 receives the operation content selected from the operation content selector 270 and receives the recognition result of the situations around the distal end portion from the recognition unit 264. Here, the operation content selector 270 selects the "advance operation PSS" of advancing the distal end portion 12 as the operation content, and the recognition unit 264 recognizes that a region where the endoscope can be advanced exists in sub (3,2) existing at a position higher than a central part of the endoscopic image. Since sub (3,2) exists above the advancing direction of the distal end portion of the endoscope, the operation content determiner 271 determines that the advance operation PSS selected by the operation content selector 270 is not appropriate. In a case where it is determined that the selected advance operation PSS is not appropriate, the operation content determiner 271 may forcibly end (interrupt) automated control of the operation of the endoscope 10.

At this time, the operation content determiner 271 may determine the "angle operation UPS" for bending the bent portion 13 and directing the distal end portion 12 in the upward direction as the operation content to be performed. Alternatively, the operation content determiner 271 may determine that the "advance operation PSS" is performed after the "angle operation UPS" as the operation content to be performed. In this manner, the operation content determiner 271 determines whether or not the operation content selected by the operation content selector 270 is appropriate based on the recognition result by the recognition unit 264, thereby correcting the operation content inappropriate for the situations of the distal end portion of the endoscope.

Figures 35A, 35B:
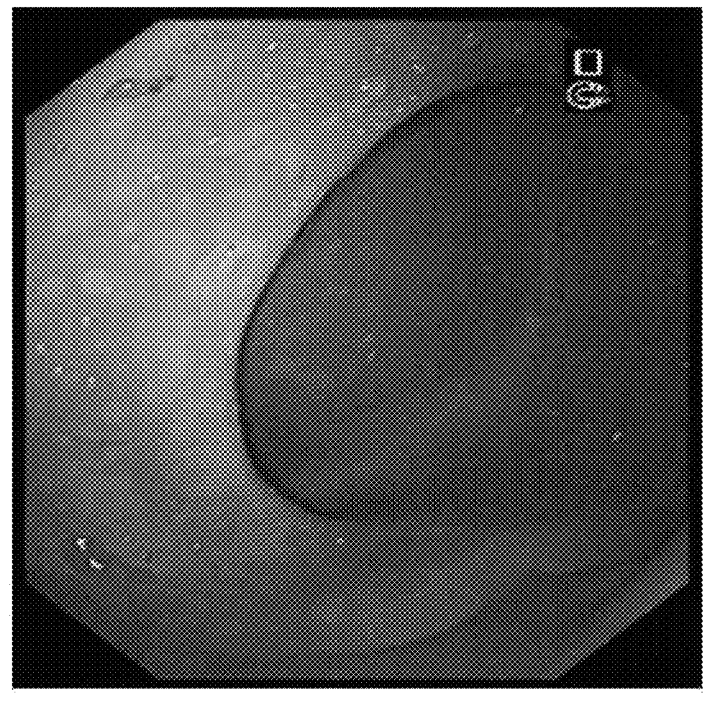
FIG. 35(*a*) is a view illustrating an example of an endoscopic image, and FIG. 35(*b*) is a view illustrating an example of a segmentation result image.

FIG. 35(*a*) illustrates another example of an endoscopic image. When acquiring an endoscopic image photographed by the endoscope 10 from the signal processor 220, the image acquisition unit 261 supplies the endoscopic image to the operation content selector 270 and the segmentation unit 262. It is assumed that, as a result of inputting the input data acquired from the endoscopic image of FIG. 35(*a*) to the operation selection model 272, the operation content selector 270 selects the "advance operation PSS" of advancing the distal end portion 12 as the operation content. The operation content selector 270 supplies the selected operation content to the operation content determiner 271.

FIG. 35(*b*) illustrates an example of a segmentation result by the segmentation unit 262. The segmentation unit 262 generates a segmentation result image and supplies the segmentation result image to the recognition unit 264. The recognition unit 264 divides the segmentation result image into 5×5 partial regions, and recognizes the proportion of the normal lumen region included in each partial region.

Figure 36:
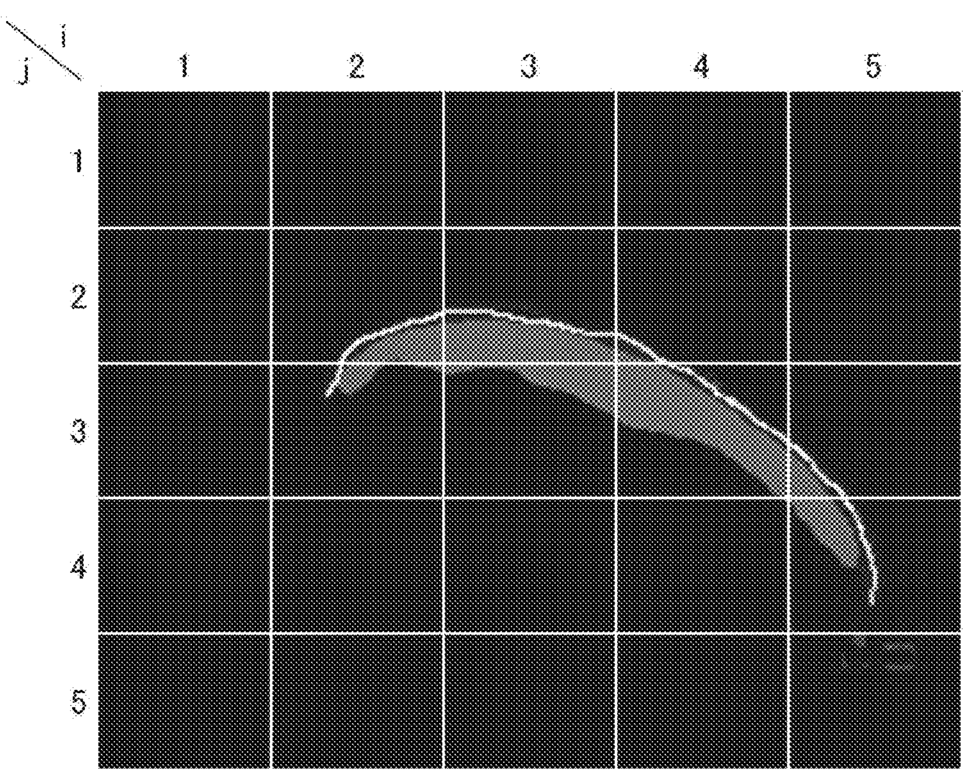
FIG. 36 is a diagram illustrating a state in which the segmentation result image is divided into a plurality of partial regions.

FIG. 36 illustrates a state in which the segmentation result image is divided into a plurality of partial regions. In this example, the region extracted as the normal lumen does not exist, and the region of the fold edge of the bent portion and the region of the lumen of the bent portion along the fold edge of the bent portion are extracted. The recognition unit 264 recognizes that no normal lumen region exists in each partial region sub (i,j) and that a lumen region of the bent portion exists.

First, the recognition unit 264 extracts a partial region that includes the lumen of the bent portion and the extracted region. In this example, the recognition unit 264 recognizes that the lumen region of the bent portion exists across the partial regions sub (2,2), sub (3,2), sub (4,2), sub (2,3), sub (3,3), sub (4,3), sub (5,3), and sub (5,4). From this, the recognition unit 264 recognizes that the lumen region of the bent portion exists in the central part in the vertical direction.

Subsequently, the recognition unit 264 extracts pixels of the fold edge of the bent portion, and specifies the orientation of an arc of the lumen of the bent portion from two end points and a midpoint thereof.

Figure 37:
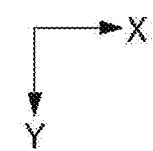
FIG. 37 is a diagram illustrating two end points of a fold edge of a bent portion and a midpoint thereof.
Figure 37:
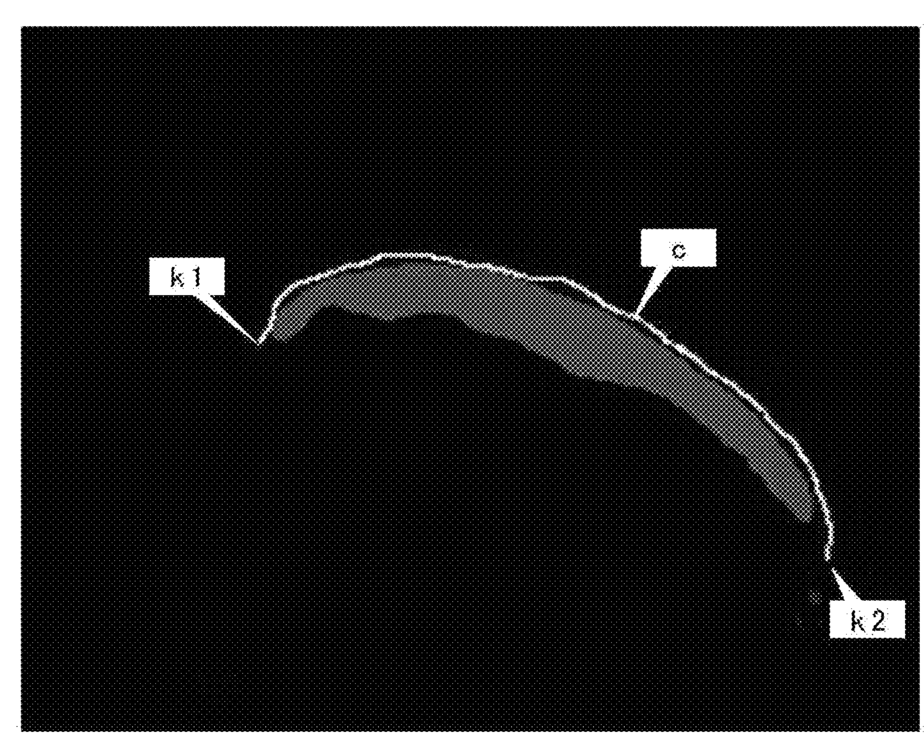

FIG. 37 illustrates two end points of the fold edge of the bent portion and the midpoint thereof. The recognition unit 264 specifies the orientation of the arc formed by the fold edge of the bent portion by specifying the orientation of a perpendicular line descending from a midpoint c relative to a line segment connecting the two end points k1 and k2. In this example, since the perpendicular line can be drawn in the downward left direction from the midpoint c relative to the line segment connecting the end points k1 and k2, the recognition unit 264 recognizes that the fold edge of the bent portion has an opening that faces the downward left direction relative to the midpoint c, that is, the extending direction of the lumen is the upward right direction of the endoscopic image.

As described above, from the segmentation result image shown in FIG. 37, the recognition unit 264 recognizes that the bent portion of the lumen exists at substantially the central portion of the endoscopic image and the extending direction of the lumen is the upward right direction of the image, and supplies the recognition result to the operation content determiner 271.

When receiving the recognition result from the recognition unit 264, the operation content determiner 271 determines that the advance operation PSS selected by the operation content selector 270 is not appropriate. From the recognition result, the operation content determiner 271 confirms that the operation of directing the distal end portion 12 to the downward left relative to the bent portion is preferable. Therefore, the operation content determiner 271 may determine the "angle operation DLS" for bending the bent portion 13 and directing the distal end portion 12 in the downward left direction as the operation content to be performed. Alternatively, the operation content determiner 271 may determine that the "advance operation PSS" is performed after the "angle operation DLS" as the operation content to be performed. In this manner, the operation content determiner 271 determines whether or not the operation content selected by the operation content selector 270 is appropriate based on the recognition result by the recognition unit 264, thereby correcting the operation content inappropriate for the situations of the distal end portion of the endoscope.

The method has been described above in which the operation content determiner 271 determines whether or not the operation content selected by the operation content selector 270 is appropriate based on the result of the recognition unit 264 recognizing a region analysis result by the segmentation unit 262. Hereinafter, a method will be described in which the operation content determiner 271 determines whether or not the operation content selected by the operation content selector 270 is appropriate by further taking into account the depth information of the endoscopic image generated by the depth information generator 263.

Figure 38:
FIG. 38 is a view illustrating another example of an endoscopic image.

FIG. 38 illustrates another example of an endoscopic image. In a lower part of the endoscopic image, the lumen is linearly photographed in the depth direction, and a plurality of folds exists surrounding the lumen. When acquiring an endoscopic image photographed by the endoscope 10 from the signal processor 220, the image acquisition unit 261 supplies the endoscopic image to the operation content selector 270, the segmentation unit 262, and the depth information generator 263. It is assumed that, as a result of inputting the input data acquired from the endoscopic image of FIG. 38 to the operation selection model 272, the operation content selector 270 selects the "angle operation DOS" of bending the bent portion 13 and directing the distal end portion 12 in the downward direction as the operation content. The operation content selector 270 supplies the selected operation content to the operation content determiner 271.

Figure 39:
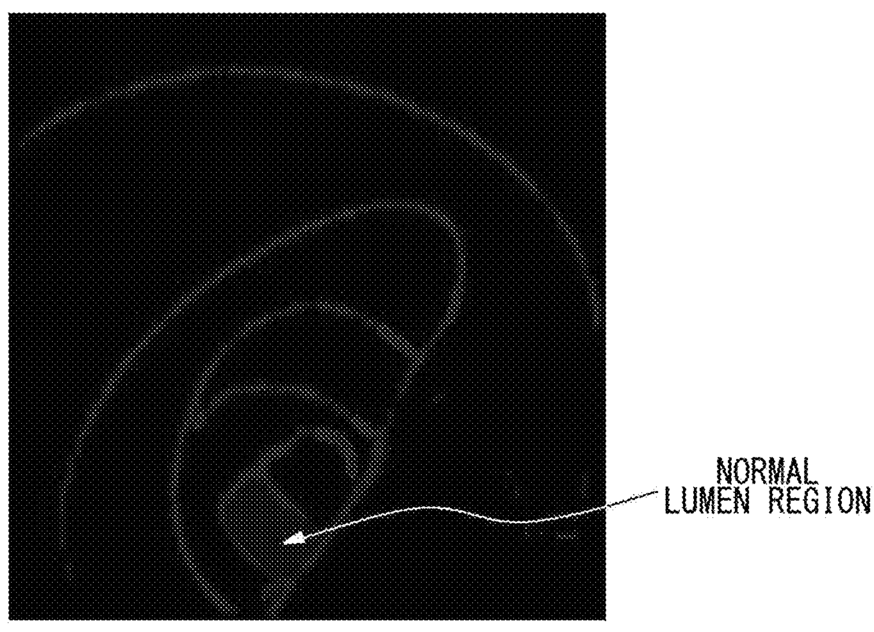
FIG. 39 is a diagram illustrating an example of a segmentation result.

FIG. 39 illustrates an example of a segmentation result by the segmentation unit 262. The segmentation unit 262 partitions the endoscopic image into a plurality of regions, derives region information indicating the result of the segmentation, and generates a segmentation result image. The segmentation result image shown in FIG. 39 includes a region of a fold edge and a region of a normal lumen. The segmentation unit 262 supplies the segmentation result image to the recognition unit 264 as the region information indicating the result of the segmentation.

Figure 40:
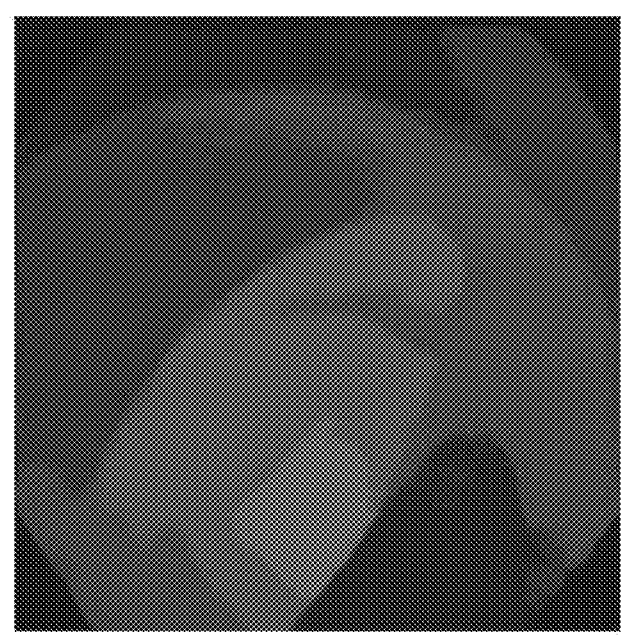
FIG. 40 is a diagram illustrating an example of a depth information estimation result.

FIG. 40 illustrates an example of a depth information estimation result by the depth information generator 263. The depth information generator 263 executes the depth estimation processing on the endoscopic image to generate depth information indicating the depth of the endoscopic image, and generates a depth estimation result image. The depth information generator 263 supplies the depth estimation result image to the recognition unit 264 as the depth information of the endoscopic image.

The recognition unit 264 receives the region information of the endoscopic image from the segmentation unit 262, receives the depth information of the endoscopic image from the depth information generator 263, and recognizes the situations around the distal end portion of the endoscope.

Figure 41:
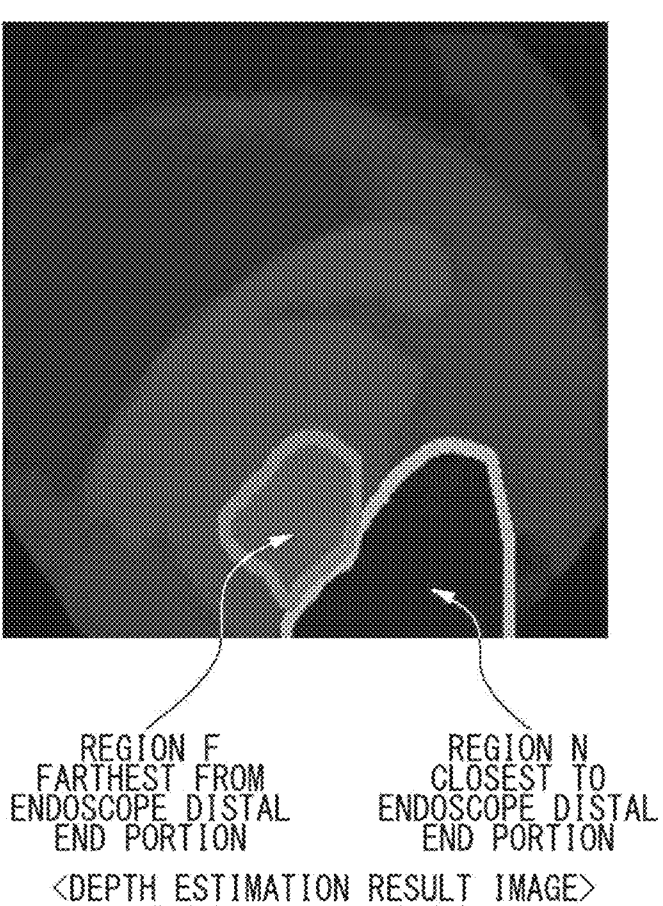
FIG. 41 is a diagram illustrating a recognition example of the depth estimation result image.

FIG. 41 illustrates a recognition example of the depth estimation result image. The recognition unit 264 recognizes that the normal lumen region exists in a lower center of the image from the segmentation result image. Further, from the depth estimation result image, the recognition unit 264 recognizes that a region N closest to the distal end portion of the endoscope exists in the lower right of the image, and a region F farthest from the distal end portion of the endoscope exists adjacent to the region N. Further, the recognition unit 264 refers to the segmentation result image and the depth estimation result image to recognize that a fold edge region exists at the boundary between the region N and the region F, and the normal lumen region exists in the region F.

As described above, from the segmentation result image shown in FIG. 39 and the depth estimation result image shown in FIG. 40, the recognition unit 264 recognizes that the normal lumen region exists in the lower center of the endoscopic image and a fold region very close to the endoscope distal end is adjacent to the right side of the normal lumen region, and supplies the recognition result to the operation content determiner 271.

The operation content determiner 271 receives the operation content selected from the operation content selector 270 and receives the recognition result of the situations around the distal end portion from the recognition unit 264. Here, the operation content determiner 271 selects the "angle operation DOS" of directing the distal end portion 12 in the downward direction as the operation content. From the recognition result received from the recognition unit 264, the operation content determiner 271 confirms that a fold that may come into contact when the distal end portion 12 is directed in the downward direction exists in a lower right portion of the endoscopic image. The operation content determiner 271 may grasp in advance that the fold region to which the label value d0 is assigned is likely to come into contact. Therefore, the operation content determiner 271 determines that the angle operation DOS selected by the operation content selector 270 is not appropriate, and changes the operation content to the angle operation DLS of directing the distal end portion 12 in the downward left direction. Note that, the operation content determiner 271 may determine the operation content of advancing after performing the angle operation in the upward direction so as to pass over the fold existing in the lower right.

The method has been described above in which the operation content determiner 271 determines whether or not the operation content selected by the operation content selector 270 is appropriate based on the result that the recognition unit 264 recognizes the region analysis result by the segmentation unit 262 and the depth estimation processing result by the depth information generator 263. In another example, the operation content determiner 271 can also determine whether or not the operation content selected by the operation content selector 270 is appropriate based on the result that the recognition unit 264 recognizes the depth estimation processing result by the depth information generator 263. As described above, in Example 2, the operation content determiner 271 may determine whether or not the operation content selected by the operation content selector 270 is appropriate based on the recognized situations around the distal end portion of the endoscope by the recognition unit 264.

The present disclosure has been described above based on a plurality of examples. It is to be understood by those skilled in the art that these embodiments and examples are illustrative, that various modifications can be made to combinations of each component and each processing process, and that such modifications are also within the scope of the present disclosure. In the examples, image processing when the endoscope 10 is inserted into the large intestine has been described, but the endoscope 10 may be inserted into another organ or may be inserted into a pipe or the like.

In the examples, an example has been described in which the motion content or operation content of the endoscope 10 is determined by processing the endoscopic image and automated insertion control is applied. In a modification, the determined motion content or operation content may be displayed on the display device 60 as guide information when the physician manually operates the endoscope 10. Further, the determined motion content or operation content may be recorded as log information.

What is claimed is:

1. An endoscopic image processing apparatus comprising:

one or more processors comprising hardware, wherein the one or more processors being configured to:

acquire an endoscopic image photographed by an endoscope;

partition the acquired endoscopic image into a plurality of regions corresponding to a plurality of structures of a subject;

generate depth information indicating a depth of the acquired endoscopic image;

recognize a region corresponding to a lumen inside the subject and a region corresponding to a structure different from the lumen together with a positional relationship in a depth direction based on region information indicating a result of segmentation into the plurality of regions corresponding to the plurality of structures and the depth information of the endoscopic image; and specify a direction in which the endoscope is advanceable based on the region corresponding to the lumen inside the subject and the region corresponding to the structure different from the lumen.

2. The endoscopic image processing apparatus according to claim 1, wherein one of the regions of the plurality of structures is a region in which the endoscope is advanceable; and the one or more processors being configured to recognize that a region corresponding to a structure existing in front of the region corresponding to the lumen in which the endoscope is advanceable is a region corresponding to a structure that obstructs the advancement of the endoscope.

3. The endoscopic image processing apparatus according to claim 2, wherein the one or more processors being configured to:

specify a direction in which the endoscope is advanceable and a direction in which the endoscope should not be advanced based on the region corresponding to the lumen in which the endoscope is advanceable and the region corresponding to the structure that obstructs the advancement of the endoscope; and generate information on an advancing direction of the endoscope based on the direction in which the endoscope is advanceable and the direction in which the endoscope should not be advanced.

4. An endoscopic image processing apparatus, comprising:

one or more processors comprising hardware, wherein the one or more processors being configured to:

acquire an endoscopic image photographed by an endoscope;

select one or more operation contents from a plurality of predetermined operation contents based on the acquired endoscopic image;

partition the acquired endoscopic image into a plurality of regions corresponding to a plurality of structures of a subject;

recognize a region corresponding to a lumen and a region corresponding to a structure different from the lumen around a distal end portion of the endoscope based on region information indicating a result of segmentation;

determine whether or not the selected one or more operation contents are appropriate based on a result of the recognition; and change the selected one or more operation contents if the selected one or more operation contents are determined to be not appropriate.

5. The endoscopic image processing apparatus according to claim 4, wherein the one or more processors being configured to when an advance operation for advancing the endoscope is selected and if the selected advance operation is determined to be not appropriate, change the advance operation to a different operation content.

6. The endoscopic image processing apparatus according to claim 4, wherein the one or more processors being configured to select the one or more operation contents by inputting input data acquired from the acquired endoscopic image to one or more operation selection models generated by machine learning that uses, as supervised data, learning images that are endoscopic images photographed in the past and labels that indicate operation contents for the endoscopes that have photographed the learning images.

7. The endoscopic image processing apparatus according to claim 4, wherein the one or more processors being configured to:

generate depth information indicating a depth of the acquired endoscopic image, recognize a region corresponding to a lumen and a region corresponding to a structure different from the lumen together with a positional relationship in a depth direction based on region information indicating a result of segmentation and the depth information of the endoscopic image; and specify a direction in which the endoscope is advanceable based on the region corresponding to the lumen and the region corresponding to the structure different from the lumen.

8. A method of processing an endoscopic image comprising:

acquiring an endoscopic image photographed by an endoscope;

partitioning the acquired endoscopic image into a plurality of regions corresponding to a plurality of structures of a subject;

generating depth information indicating a depth of the acquired endoscopic image;

recognizing a region corresponding to a lumen inside the subject and a region corresponding to a structure different from the lumen together with a positional relationship in a depth direction based on region information indicating a result of segmentation into the plurality of regions corresponding to the plurality of structures and the depth information of the endoscopic image; and specifying a direction in which the endoscope is advanceable based on the region corresponding to the lumen inside the subject and the region corresponding to the structure different from the lumen.

9. A computer program storage medium that stores programs, wherein the programs cause a computer to implement:

a function of acquiring an endoscopic image photographed by an endoscope;

a function of partitioning the acquired endoscopic image into a plurality of regions corresponding to a plurality of structures of a subject;

a function of generating depth information indicating a depth of the acquired endoscopic image;

a function of recognizing a region corresponding to a lumen inside the subject and a region corresponding to a structure different from the lumen together with a positional relationship in a depth direction based on region information indicating a result of segmentation into the plurality of regions corresponding to the plurality of structures and the depth information of the endoscopic image; and a function of specifying a direction in which the endoscope is advanceable based on the region corresponding to the lumen inside the subject and the region corresponding to the structure different from the lumen.

10. The endoscopic image processing apparatus according to claim 4, wherein the one or more processors being configured to:

define a region having a structure of a class, which is a type of a region to be divided, and generate a region division result obtained by assigning label values to pixels of various structures of the subject.

11. The endoscopic image processing apparatus according to claim 4, wherein the one or more processors being configured to:

set a class in accordance with a distance range from a distal end portion of the endoscope; and generate depth information in which a label value is assigned to a pixel corresponding to the class.

* * * * *